US012721613B2

(12) United States Patent
Vidmar et al.

(10) Patent No.: US 12,721,613 B2
(45) Date of Patent: Sep. 1, 2026

(54) RETRACTOR

(71) Applicant: Spinal Elements, Inc., Carlsbad, CA (US)

(72) Inventors: Stephen Vidmar, Carlsbad, CA (US); Evan Ackema, Oceanside, CA (US); Darren Reimers, Carlsbad, CA (US); David Ortiz, Carlsbad, CA (US); Kellen Van Ausdal, Franklin, TN (US); Ricardo Simmons, San Diego, CA (US); Abhishek Kumar, New York, NY (US); Douglas Crowther, Colorado Springs, CO (US); Sandeep Kunwar, Woodside, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 216 days.

(21) Appl. No.: 18/339,600

(22) Filed: Jun. 22, 2023

(65) Prior Publication Data

US 2024/0008863 A1 Jan. 11, 2024

Related U.S. Application Data

(60) Provisional application No. 63/355,293, filed on Jun. 24, 2022.

(51) Int. Cl.
*A61B 17/02* (2006.01)

(52) U.S. Cl.
CPC ................................ *A61B 17/0206* (2013.01)

(58) Field of Classification Search
CPC .. A61B 17/02; A61B 17/0206; A61B 17/0218
See application file for complete search history.

(56) References Cited

U.S. PATENT DOCUMENTS 350,721 A 10/1886 Cooper
569,839 A 10/1896 Roeloffs
(Continued)

FOREIGN PATENT DOCUMENTS

EP 2 705 799 3/2014
JP 2010-508978 3/2010
(Continued)

OTHER PUBLICATIONS

Dimension®, MIS TLIF Retractor System, Spinal Elements, https://spinalelements.com/products/access-systems/dimension/, 2023, pp. 1.

(Continued)

*Primary Examiner* — Si Ming Ku
(74) *Attorney, Agent, or Firm* — Knobbe, Martens, Olson & Bear, LLP

(57) ABSTRACT

A retractor for use in surgical operations can include a first blade assembly comprising a first blade, a first actuator configured to translate the first blade along a first translation direction, a first lock handle configured to limit translation along a direction opposite the first translation direction. The retractor can include a second blade assembly comprising a second blade. The method can include providing a retractor comprising a first blade assembly comprising a first blade, a first actuator, a first lock handle, and second blade assembly comprising a second blade. The method can include translating the first blade along a first translation direction with the first actuator. The first lock handle can limit translation along a direction opposite the first translation direction.

20 Claims, 34 Drawing Sheets

(56) References Cited

U.S. PATENT DOCUMENTS

| | | | |
|---|---|---|---|
| 1,311,313 | A | 7/1919 | Brix |
| 1,328,624 | A | 1/1920 | Graham |
| 1,613,141 | A | 1/1927 | Stein |
| 1,822,280 | A | 9/1931 | Ervay |
| 2,002,021 | A | 5/1935 | Rouse |
| 2,670,731 | A | 3/1954 | Zoll et al. |
| 2,693,795 | A | 11/1954 | Grieshaber |
| 2,850,008 | A | 9/1958 | Resch |
| 3,168,093 | A | 2/1965 | Gauthier |
| 3,384,078 | A | 5/1968 | Gauthier |
| 3,522,799 | A | 8/1970 | Gauthier |
| 3,747,592 | A | 7/1973 | Santos |
| 3,782,370 | A | 1/1974 | McDonald |
| 3,965,890 | A | 6/1976 | Gauthier |
| 4,156,424 | A | 5/1979 | Burgin |
| 4,616,635 | A | 10/1986 | Caspar et al. |
| 4,667,657 | A | 5/1987 | Kulik et al. |
| 5,035,232 | A | 7/1991 | Lutze et al. |
| 5,113,846 | A | 5/1992 | Hiltebrandt et al. |
| 5,363,841 | A | 11/1994 | Coker |
| 5,618,260 | A | 4/1997 | Caspar et al. |
| 5,681,265 | A | 10/1997 | Maeda et al. |
| 5,772,583 | A | 6/1998 | Wright et al. |
| 5,928,139 | A | 7/1999 | Koros et al. |
| 5,931,777 | A | 8/1999 | Sava |
| 5,931,778 | A | 8/1999 | Furnish |
| 5,980,455 | A | 11/1999 | Daniel et al. |
| 6,042,540 | A | 3/2000 | Johnston et al. |
| 6,074,343 | A | 6/2000 | Nathanson et al. |
| 6,080,155 | A | 6/2000 | Michelson |
| 6,139,493 | A | 10/2000 | Koros et al. |
| 6,206,826 | B1 | 3/2001 | Mathews et al. |
| 6,264,650 | B1 | 7/2001 | Hovda et al. |
| 7,087,055 | B2 | 8/2006 | Lim et al. |
| 7,229,408 | B2 | 6/2007 | Douglas et al. |
| 7,390,298 | B2 | 6/2008 | Chu |
| 7,481,766 | B2 | 1/2009 | Lee et al. |
| 7,491,168 | B2 | 2/2009 | Raymond et al. |
| 7,537,565 | B2 | 5/2009 | Bass |
| 7,582,058 | B1 | 9/2009 | Miles et al. |
| 7,594,888 | B2 | 9/2009 | Raymond et al. |
| 7,691,057 | B2 | 4/2010 | Miles |
| 7,722,613 | B2 | 5/2010 | Sutterlin et al. |
| 7,785,253 | B1 | 8/2010 | Arambula et al. |
| 7,819,801 | B2 | 10/2010 | Miles et al. |
| 7,846,183 | B2 | 12/2010 | Blain |
| 7,892,173 | B2 | 2/2011 | Miles et al. |
| 7,905,840 | B2 | 3/2011 | Pimenta |
| 7,922,658 | B2 | 4/2011 | Cohen et al. |
| 8,062,217 | B2 | 11/2011 | Boucher et al. |
| 8,062,218 | B2 | 11/2011 | Sebastian et al. |
| 8,137,284 | B2 | 3/2012 | Miles et al. |
| 8,142,355 | B2 | 3/2012 | Blain et al. |
| 8,192,356 | B2 | 6/2012 | Miles et al. |
| 8,303,498 | B2 | 11/2012 | Miles et al. |
| 8,303,515 | B2 | 11/2012 | Miles et al. |
| 8,313,430 | B1 | 11/2012 | Pimenta |
| 8,353,826 | B2 | 1/2013 | Weiman |
| 8,388,527 | B2 | 3/2013 | Miles et al. |
| 8,409,091 | B2 | 4/2013 | Blain et al. |
| 8,500,634 | B2 | 8/2013 | Miles et al. |
| 8,523,768 | B2 | 9/2013 | Miles et al. |
| 8,556,808 | B2 | 10/2013 | Miles et al. |
| 8,628,469 | B2 | 1/2014 | Miles et al. |
| 8,663,102 | B2 | 3/2014 | Michaeli et al. |
| 8,740,786 | B2 | 6/2014 | Blain et al. |
| 8,753,270 | B2 | 6/2014 | Miles et al. |
| 8,753,271 | B1 | 6/2014 | Miles et al. |
| 8,821,396 | B1 | 9/2014 | Miles et al. |
| 8,876,687 | B2 | 11/2014 | Jones et al. |
| 8,876,904 | B2 | 11/2014 | Pimenta et al. |
| 8,915,846 | B2 | 12/2014 | Miles et al. |
| 8,945,004 | B2 | 2/2015 | Miles et al. |
| 8,986,344 | B2 | 3/2015 | Sandhu |
| 9,028,522 | B1 | 5/2015 | Prado |
| 9,044,280 | B1 | 6/2015 | Arambula et al. |
| 9,050,146 | B2 | 6/2015 | Woolley et al. |
| 9,066,701 | B1 | 6/2015 | Finley |
| 9,138,217 | B2 | 9/2015 | Smith et al. |
| 9,220,491 | B2 | 12/2015 | Nunley et al. |
| 9,265,490 | B2 | 2/2016 | Bowman et al. |
| 9,351,718 | B1 | 5/2016 | Arambula et al. |
| 9,387,009 | B2 | 7/2016 | Fatone |
| 9,408,596 | B2 | 8/2016 | Blain |
| 9,414,831 | B2 | 8/2016 | Sandhu |
| 9,451,940 | B2 | 9/2016 | Spann |
| 9,456,846 | B2 | 10/2016 | Predick |
| 9,468,405 | B2 | 10/2016 | Miles et al. |
| 9,486,133 | B2 | 11/2016 | Lee et al. |
| 9,572,560 | B2 | 2/2017 | Msat |
| 9,585,649 | B2 | 3/2017 | Blain et al. |
| 9,610,071 | B2 | 4/2017 | Miles et al. |
| 9,615,818 | B2 | 4/2017 | Baudouin et al. |
| 9,622,732 | B2 | 4/2017 | Martinelli et al. |
| 9,649,101 | B2 | 5/2017 | Karpowicz et al. |
| 9,693,761 | B2 | 7/2017 | Fedorov et al. |
| 9,693,762 | B2 | 7/2017 | Reimels |
| 9,693,763 | B2 | 7/2017 | Blain |
| 9,737,288 | B2 | 8/2017 | Karpowicz et al. |
| 9,750,490 | B2 | 9/2017 | Miles et al. |
| 9,782,158 | B2 | 10/2017 | Nunley et al. |
| 9,788,822 | B2 | 10/2017 | Miles et al. |
| 9,795,371 | B2 | 10/2017 | Miles et al. |
| 9,820,729 | B2 | 11/2017 | Miles et al. |
| 9,826,966 | B2 | 11/2017 | Mast et al. |
| 9,826,968 | B2 | 11/2017 | Miles et al. |
| 9,833,227 | B2 | 12/2017 | Miles et al. |
| 9,848,863 | B2 | 12/2017 | Cryder et al. |
| 9,861,273 | B2 | 1/2018 | Weiman |
| 9,943,301 | B2 | 4/2018 | Mast et al. |
| 10,039,539 | B2 | 8/2018 | Friedrich et al. |
| 10,076,320 | B2 | 9/2018 | Mast et al. |
| 10,085,854 | B2 | 10/2018 | Spann |
| 10,166,018 | B2 | 1/2019 | Hunt |
| 10,172,603 | B2 | 1/2019 | Blain |
| 10,178,987 | B2 | 1/2019 | Predick |
| 10,299,777 | B2 | 5/2019 | Mast et al. |
| 10,383,613 | B2 | 8/2019 | Daavettila et al. |
| 10,426,450 | B2 | 10/2019 | Vogel et al. |
| 10,532,197 | B2 | 1/2020 | Predick |
| D882,781 | S | 4/2020 | Rustamzadeh |
| 10,898,174 | B2 | 1/2021 | Blain |
| 10,945,861 | B2 | 3/2021 | Abdou |
| 10,973,505 | B2 | 4/2021 | Ortiz et al. |
| 11,179,146 | B2 | 11/2021 | Vogel et al. |
| D956,224 | S | 6/2022 | Gregersen et al. |
| D956,225 | S | 6/2022 | Gregersen et al. |
| 11,589,858 | B2 | 2/2023 | Berry |
| 11,801,042 | B2 | 10/2023 | Blain |
| 12,226,087 | B2 | 2/2025 | Ortiz et al. |
| 12,226,088 | B2 | 2/2025 | Ortiz et al. |
| 12,232,713 | B2 | 2/2025 | Vogel et al. |
| 12,465,346 | B2 | 11/2025 | Blain |
| 2002/0123668 | A1 | 9/2002 | Ritland |
| 2005/0102029 | A1 | 5/2005 | Blain |
| 2005/0107877 | A1 | 5/2005 | Blain |
| 2005/0137461 | A1 | 6/2005 | Marchek |
| 2005/0159650 | A1 | 7/2005 | Raymond et al. |
| 2005/0159651 | A1 | 7/2005 | Raymond et al. |
| 2005/0159818 | A1 | 7/2005 | Blain |
| 2005/0192574 | A1 | 9/2005 | Blain |
| 2006/0004261 | A1 | 1/2006 | Douglas |
| 2006/0074278 | A1 | 4/2006 | Petit et al. |
| 2006/0074425 | A1 | 4/2006 | Sutterlin et al. |
| 2006/0106416 | A1 | 5/2006 | Raymond et al. |
| 2006/0224044 | A1 | 10/2006 | Marchek et al. |
| 2006/0235423 | A1 | 10/2006 | Cantu |
| 2007/0100212 | A1 | 5/2007 | Pimenta et al. |
| 2007/0185376 | A1 | 8/2007 | Wilson et al. |
| 2007/0238932 | A1 | 10/2007 | Jones et al. |
| 2008/0097164 | A1 | 4/2008 | Miles et al. |
| 2008/0114208 | A1 | 5/2008 | Hutton et al. |
| 2008/0132766 | A1 | 6/2008 | Dant et al. |
| 2008/0188718 | A1 | 8/2008 | Spitler et al. |

(56) References Cited

U.S. PATENT DOCUMENTS

2009/0018399 A1 1/2009 Martinelli
2009/0048668 A1 2/2009 Wilson et al.
2009/0259108 A1 10/2009 Miles et al.
2010/0114110 A1 5/2010 Taft et al.
2010/0174146 A1 7/2010 Miles et al.
2011/0034777 A1 2/2011 Ames et al.
2011/0130793 A1 6/2011 Woolley et al.
2011/0208226 A1 8/2011 Fatone
2011/0224497 A1 9/2011 Weiman et al.
2012/0191003 A1 7/2012 Garabedian
2012/0245432 A1 9/2012 Karpowicz et al.
2012/0283521 A1 11/2012 Smith
2013/0158359 A1* 6/2013 Predick .............. A61B 17/0206 600/224
2013/0190575 A1 7/2013 Mast et al.
2013/0261401 A1 10/2013 Hawkins et al.
2013/0274557 A1 10/2013 Bowman
2014/0024900 A1 1/2014 Capote et al.
2014/0031874 A1 1/2014 Kucharzyk
2014/0135584 A1 5/2014 Lee et al.
2014/0148652 A1 5/2014 Weiman
2014/0172002 A1 6/2014 Predick
2014/0350347 A1 11/2014 Karpowicz
2015/0051448 A1 2/2015 Hunt
2015/0088030 A1 3/2015 Taylor
2015/0230787 A1 8/2015 Friedrich et al.
2015/0250466 A1 9/2015 Thornburg
2015/0250467 A1 9/2015 Higgins
2015/0265265 A1 9/2015 Hynes
2016/0030030 A1 2/2016 Bass
2016/0317137 A1 11/2016 Predick et al.
2017/0231614 A1 8/2017 Vogel
2019/0083081 A1* 3/2019 Ortiz .................. A61B 17/0206
2019/0110785 A1* 4/2019 Serokosz ........... A61B 17/0206
2019/0125328 A1 5/2019 Blain
2021/0015514 A1 1/2021 Storli et al.
2021/0085306 A1 3/2021 Clauss et al.
2021/0169463 A1 6/2021 Blain
2021/0186576 A1 6/2021 Woolley
2021/0244398 A1 8/2021 Ortiz et al.
2022/0079573 A1 3/2022 Ortiz et al.
2022/0096072 A1 3/2022 Vogel et al.
2022/0289135 A1 9/2022 Moon et al.
2024/0156448 A1 5/2024 Blain
2025/0152155 A1 5/2025 Ortiz et al.
2025/0152156 A1 5/2025 Vogel et al.
2025/0213241 A1 7/2025 Hunt

FOREIGN PATENT DOCUMENTS

JP 2013-521896 6/2013
JP 2013-537467 10/2013
JP 2014-515646 7/2014
WO WO 2006/042241 4/2006
WO WO 2012/026981 3/2012
WO WO 2012/040206 3/2012
WO WO 2013/028571 2/2013
WO WO 2013/033630 3/2013
WO WO 2015/191836 12/2015

OTHER PUBLICATIONS

Official Communication in Australian Application No. 2015315166, dated Apr. 24, 2019.
Official Communication in Australian Application No. 2015315166, dated Aug. 15, 2019.
Official Communication in Australian Application No. 2020203261, dated Jul. 26, 2021.
Official Communication in Australian Application No. 2020203261, dated May 6, 2022.
Official Communication in Canadian Application No. 2,960,818, dated May 3, 2021.
Official Communication in European Application No. 15840714.8, dated Feb. 12, 2018.
Official Communication in European Application No. 20180562.9, dated Sep. 18, 2020.
Official Communication in Japanese Application No. 2017-513531, dated Jun. 24, 2019.
Official Communication in Japanese Application No. 2017-513531, dated May 25, 2020.
Official Communication in Japanese Application No. 2017-513531, dated Feb. 22, 2021.
Official Communication in Japanese Application No. 2017-513531, dated Sep. 6, 2021.
Official Communication in Japanese Application No. 2021-164806, dated Dec. 23, 2022.
International Search Report and Written Opinion in International Application No. PCT/US2015/049211, dated Dec. 4, 2015.
International Preliminary Report on Patentability and Written Opinion in International Application No. PCT/US2015/049211, dated Mar. 23, 2017.
Official Communication in Australian Application No. 2017228829, dated May 17, 2021.
Official Communication in Australian Application No. 2017228829, dated Feb. 23, 2022.
Official Communication in Canadian Application No. 3,015,212, dated Apr. 4, 2023. .
Official Communication in European Application No. 17763744.4, dated Nov. 12, 2019.
Invitation to Pay Additional Search Fees in International Application No. PCT/US2017/019699, dated May 24, 2017.
International Search Report and Written Opinion in International Application No. PCT/US2017/019699, dated Aug. 7, 2017.
International Preliminary Report on Patentability and Written Opinion in International Application No. PCT/US2017/019699, dated Sep. 20, 2018.
International Search Report and Written Opinion in International Application No. PCT/US2020/051031, dated Dec. 8, 2020.
International Preliminary Report on Patentability and Written Opinion in International Application No. PCT/US2020/051031, dated Mar. 31, 2022.

* cited by examiner

RETRACTOR

CROSS-REFERENCE TO RELATED APPLICATIONS

This application claims priority benefit to U.S. Provisional Patent Application No. 63/355,293, filed Jun. 24, 2022, the entirety of which is hereby incorporated by reference herein.

BACKGROUND

Field

The present application relates to surgical methods and tools, and more particularly to a retractor and a method of operating a retractor.

Description of the Related Art

Retractors are surgical devices used to spread bodily tissues in order to allow a surgeon or surgical assistant to see and access a part of the body that is to be surgically treated. In general, retractors comprise a pair of jaws or blades that grip the bodily tissue and push it apart under the force generated by an actuator, such as a pair of scissor-like arms having a distal end and a proximal end. The proximal end generally defines a pair of handles and the distal end attaches to the pair of blades so that manipulation of the handles causes the blades to move apart from one another. Once an incision is made in the body to be operated on, the blades are inserted into the incision and the actuator is manipulated to move the blades of the retractor apart, thus spreading the tissue and providing an aperture through which the surgeon can access and visualize the tissue to be surgically treated. One problem with this type of retractor is that the aperture size is generally limited by the size of the incision, meaning that a large aperture requires a relatively large incision. The drawback to this arrangement is that larger incisions result in the need for longer periods for healing of the incision. There is thus a need for a surgical retractor that is capable of creating a relatively large aperture using a relatively small incision, thereby reducing the invasiveness of the surgical procedure, post-operative healing times and patient discomfort.

SUMMARY

In some embodiments, a retractor is provided. The retractor can include a first blade assembly comprising a first blade. The retractor can include a first actuator configured to translate the first blade along a first translation direction. The retractor can include a first lock handle configured to limit translation along a direction opposite the first translation direction. The retractor can include a second blade assembly comprising a second blade.

In some embodiments, the retractor can include a second actuator configured to translate the second blade along a second translation direction. In some embodiments, the first actuator and the second actuator are configured to be rotated in the same direction to open the retractor. In some embodiments, the first actuator and the second actuator are configured to be rotated independently. In some embodiments, the retractor can include a second lock handle configured to limit translation along a direction opposite the second translation direction. In some embodiments the first blade assembly comprises a rack and the first actuator comprises a pinion. In some embodiments, the retractor can include a probe assembly comprising a first probe and a second probe. In some embodiments, the retractor can include a shim comprising an alignment feature, wherein at least one blade comprises a corresponding alignment feature. In some embodiments, the first lock handle is biased to engage a pawl with the first actuator. In some embodiments, the first lock handle pivots relative to the first actuator. In some embodiments, the first lock handle comprises a pawl configured to engage the first actuator. In some embodiments, the first lock handle is configured to limit the first blade from closing, while allowing the first blade to open along the first translation direction. In some embodiments, the first blade and the second blade are configured to move in opposite directions to open the retractor. In some embodiments, the first blade and the second blade are configured to nest when the retractor is in a closed position.

In some embodiments, a method of using a retractor is provided. The method can include providing a retractor comprising a first blade assembly comprising a first blade, a first actuator, a first lock handle, and second blade assembly comprising a second blade. The method can include translating the first blade along a first translation direction with the first actuator. In some embodiments, the first lock handle limits translation along a direction opposite the first translation direction.

In some embodiments, the method can include translating the second blade along a second translation direction with a second actuator. In some embodiments, the method can include inserting a first probe and a second probe toward an anatomical location. In some embodiments, the method can include inserting the second blade of the retractor over the first probe and the second probe. In some embodiments, the method can include removing the second probe and inserting a shim. In some embodiments, the method can include removing the first probe.

BRIEF DESCRIPTION OF THE DRAWINGS

These and other features, aspects and advantages of the described embodiments are described with reference to drawings of certain preferred embodiments, which are intended to illustrate, but not to limit. It is to be understood that the attached drawings are for the purpose of illustrating concepts of the described embodiments and may not be to scale.

DETAILED DESCRIPTION

As will be explained below, certain retractor embodiments described herein provide advantages over the prior art retractors comprising a set of blades and an actuator, such as a set of scissor arms. For example, the retractor of the illustrated embodiment allows a person to insert a relatively compact set of retractor blades into an incision having a short length. In some embodiments, the compact set of retractor blades (e.g., a first blade, a second blade) are of such a size that they can be inserted within the incision so that they are snugly embraced by the side walls of the incision (e.g., a closed position).

Optionally, an actuator causes the first blade and the second blade to move apart (e.g., to an opened position). This can cause the tissue to stretch in at least one direction, creating an opening that is substantially larger than the incision. The first actuator can be rotated to move the first blade. The second actuator can be rotated to move the second blade. The actuators can function as a rack and pinion. The retractor can include a first lock. The first lock can allow movement in a first direction. The first lock can allow movement in an opening direction of the first blade. The first lock can prevent or limit movement in another direction. The first lock can prevent or limit movement in a second direction, opposite the first direction. The first lock can prevent or limit movement in a closing direction. The retractor can include a second lock. The second lock can allow movement in a third direction. The second lock can allow movement in an opening direction of the second blade. The second lock can prevent or limit movement in another direction. The second lock can prevent or limit movement in a fourth direction, opposite the third direction. The second lock can prevent or limit movement in a closing direction. The retractor can freely open. The retractor can have an active close. The first and second actuators can be manipulated to slide or otherwise translate the first and second blades.

In certain embodiments, the retractor can be used to open up an aperture that is substantially wider and/or longer than the incision, and substantially larger than would be possible using a prior art device and/or in a manner that is easier to use and/or requiring less steps and/or less complicated steps. In certain arrangements in relative terms, the surgeon can use a smaller incision, and in some cases a much smaller incision, than would have been required with a prior art device. Moreover, in certain arrangements, removal of the retractor, e.g. by closing the blades, and removing the blades from the incision, can allow the incision to relax back to a size that is much smaller than would have resulted from use of the prior art retractor. In addition, in certain arrangements, steps performed by the surgeon to retract the tissue can be simplified, easier to use and/or involve less steps as compared to prior art devices.

Figure 1:
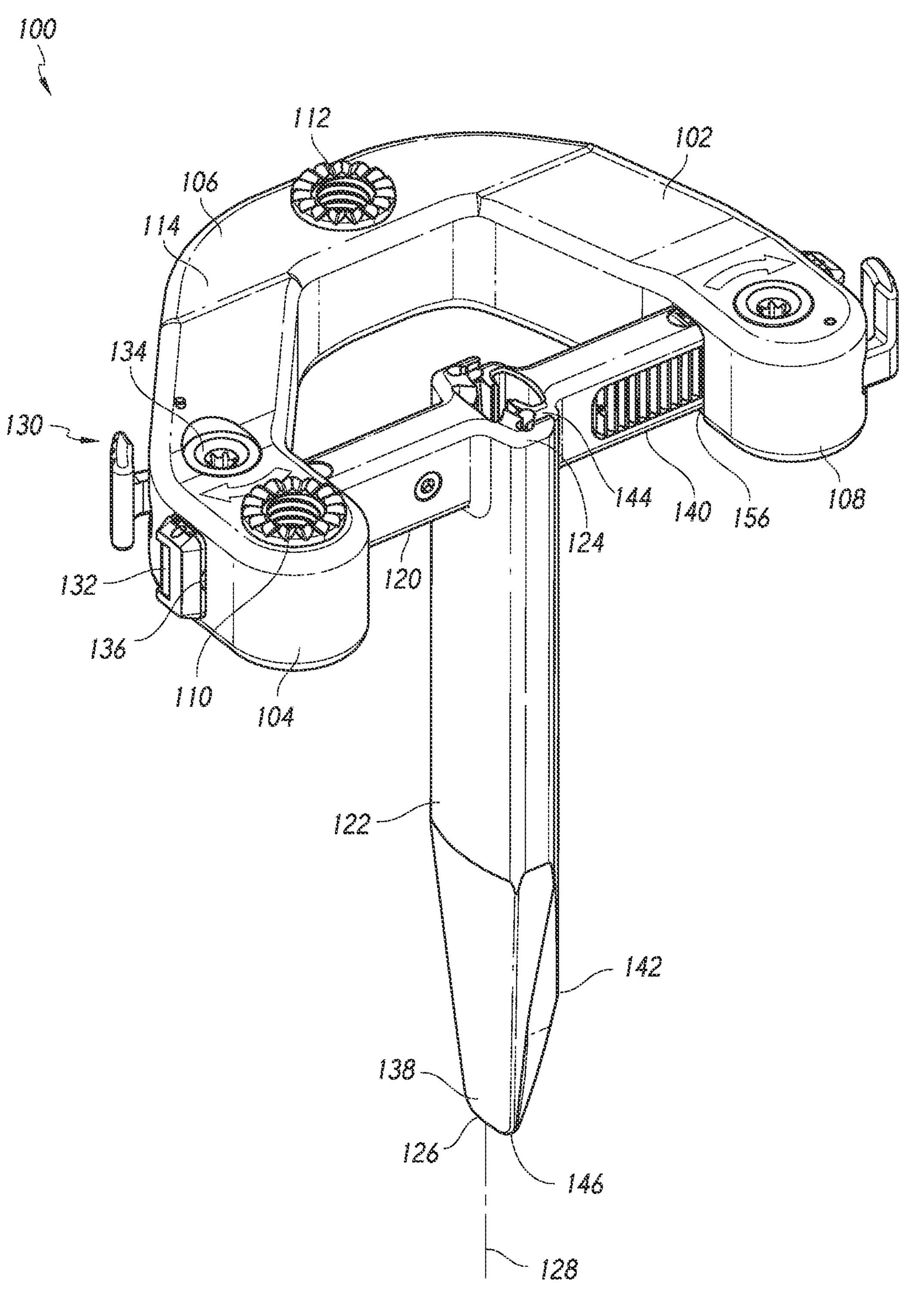
FIG. 1 provides a perspective view of an embodiment of a retractor with the blades in a closed position.
Figure 2:
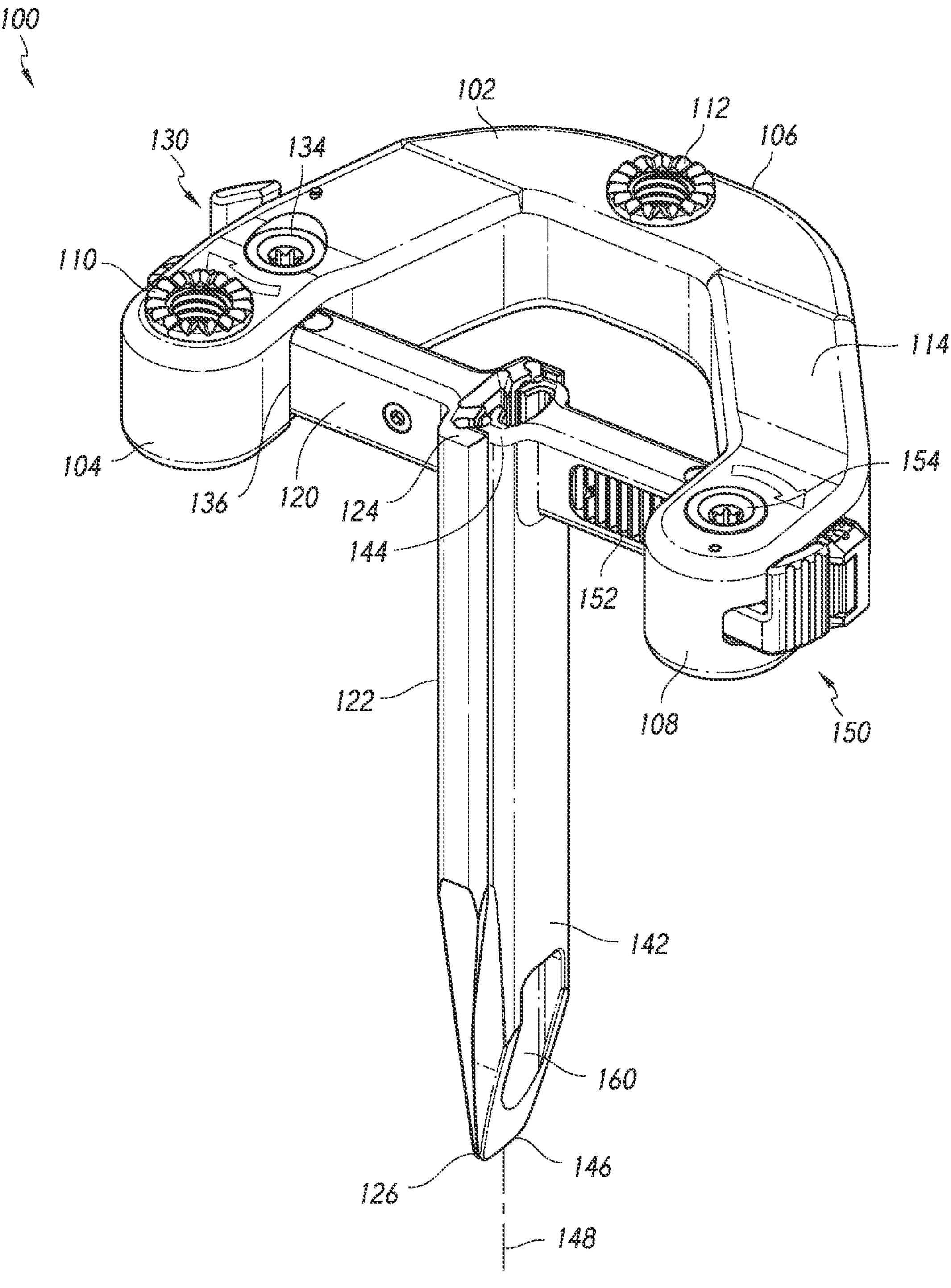
FIG. 2 provides another perspective view of the retractor of FIG. 1 with the blades in a closed position.
Figure 3:
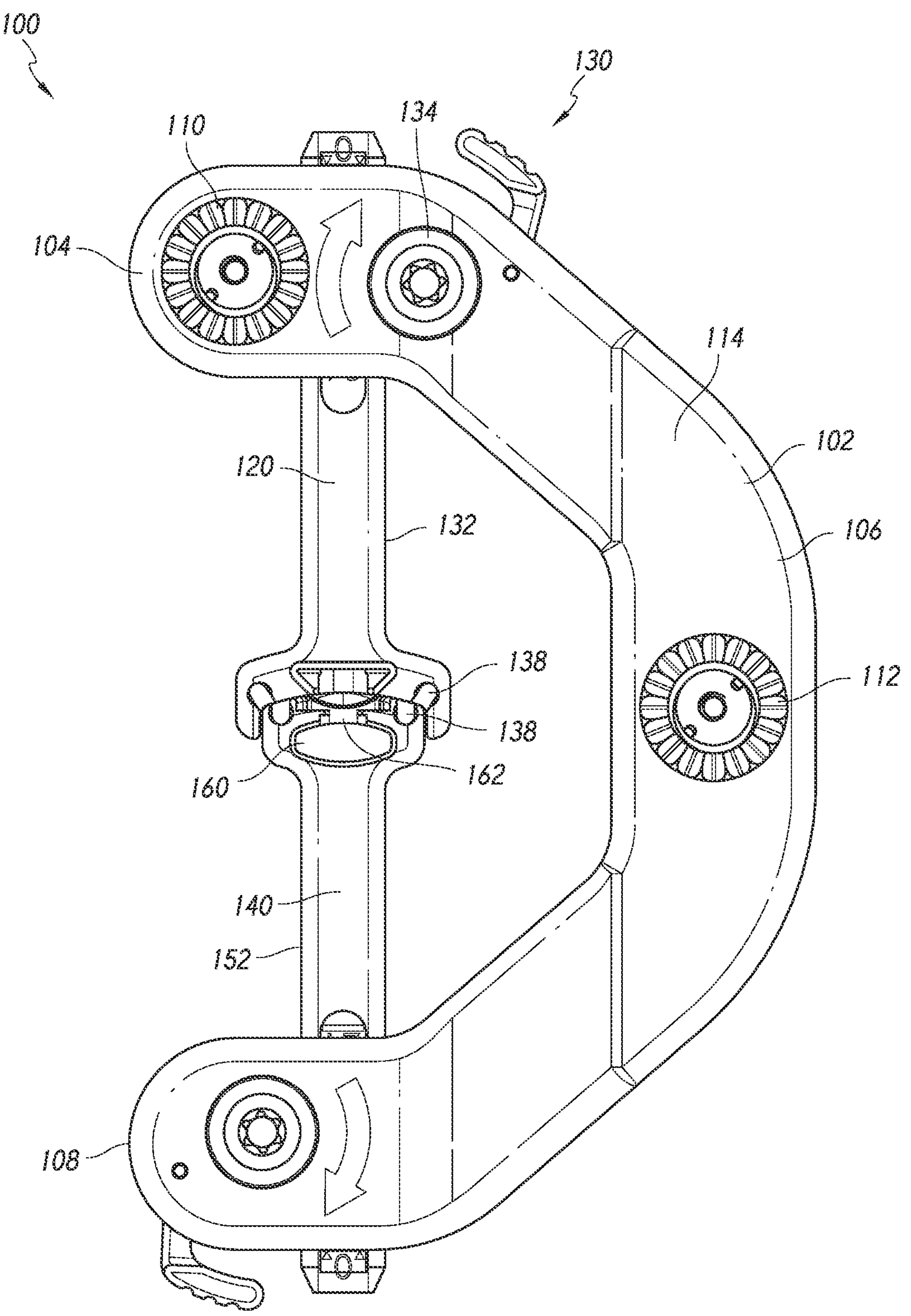
FIG. 3 provides a top view of the retractor of FIG. 1 with the blades in a closed position.
Figure 4:
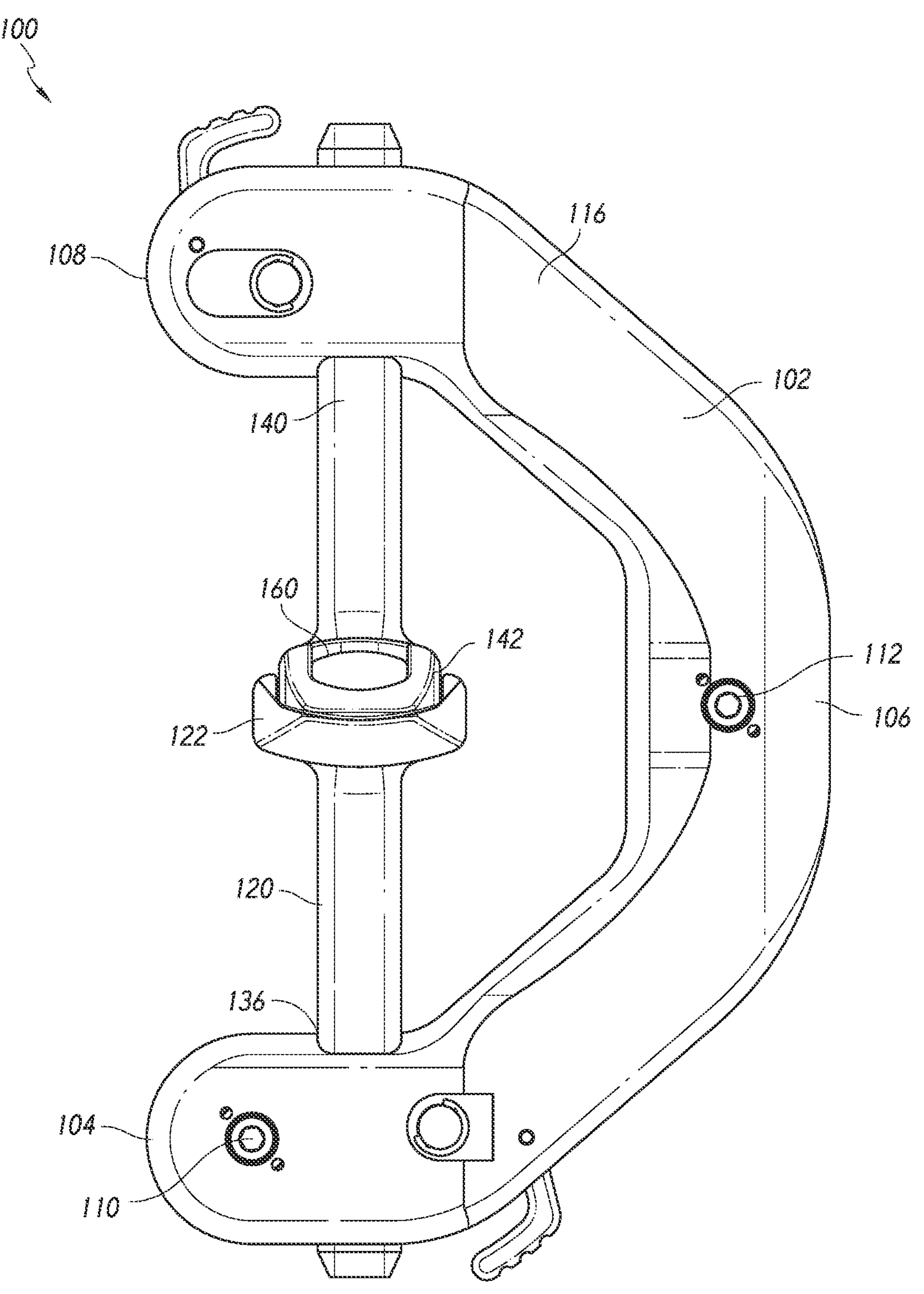
FIG. 4 provides a bottom view of the retractor of FIG. 1 with the blades in a closed position.
Figure 5:
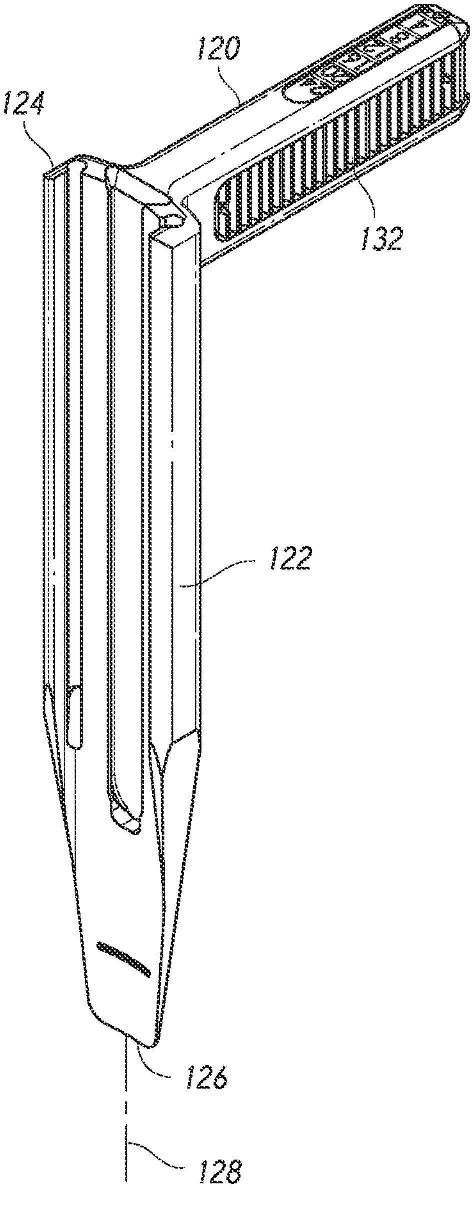
FIG. 5 provides a perspective view of an embodiment of a first blade of FIG. 1.
Figure 6:
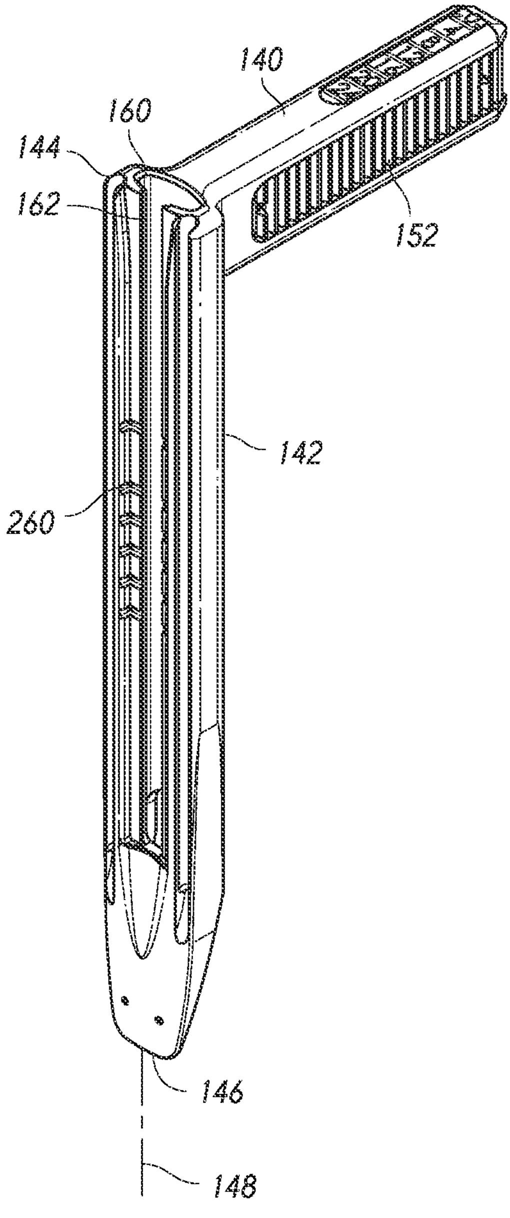
FIG. 6 provides an embodiment of a second blade of FIG. 1.

FIG. 1 illustrates a perspective view of a retractor 100 in a closed position. FIG. 2 illustrates another perspective view of the retractor 100 in a closed position. FIG. 3 illustrates a top view of the retractor 100 in a closed position. FIG. 4 illustrates a bottom view of the retractor 100 in a closed position. FIG. 5 illustrates a first blade. FIG. 6 illustrates a second blade.

The retractor 100 can include a body 102. The body 102 can include one or more linear segments. The body 102 can include one or more angled segments. The body can include one or more elevated segments. The body 102 can include one or more chamfered segments. The body 102 can be concave. The body 102 can include one or more rounded edges. The body 102 can include a portion of a polygon. The body 102 can include a portion of an octagon.

The body 102 can include a generally curved shape. The body 102 can include a first arm 104. The body 102 can include a central portion 106. The body 102 can include a second arm 108. The central portion 106 can be disposed between the first arm 104 and the second arm 108. The central portion 106 can be disposed on a different plane than the first arm 104 and the second arm 108 to accommodate patient anatomy. The first arm 104 can be parallel to the second arm 108. The body 102 can be symmetrical about the central portion 106. The first arm 104 can be a mirror image of the second arm 108. The first arm 104 and the second arm 108 can have the same features. The first arm 104 and the second arm 108 can have the same arrangement. The body 102 can be nonsymmetrical about the central portion 106. The first arm 104 and the second arm 108 can have different features. The first arm 104 and the second arm 108 can have a different arrangement.

The first arm 104 and the second arm 108 can be diametrically opposed. The first arm 104 and the second arm 108 can be parallel. The first arm 104 and the second arm 108 can be aligned. The first arm 104 and the second arm 108 can be skewed relative to each other. The first arm 104 and the second arm 108 can be spaced apart.

The retractor 100 can include one or more connectors 110, 112. The retractor 100 can include one connector, two connectors, three connectors, four connectors, or more. The body 102 can couple to one or more connectors 110, 112. The first arm 104 can couple to the connector 110. The connector 110 can be positioned near the end of the first arm 104. The central portion 106 can couple to the connector 112. The connector 112 can be centrally located. The connector 112 can be located at a neutral center of the retractor 100. The connector 112 can be positioned on a different plane than the connector 110. In some embodiments, the second arm 108 does not include a connector.

The one or more connectors 110, 112 can be located on the body 102. The one or more connectors 110, 112 couples the body 102 to a fixture (not shown). The fixture can be a surgical arm. The fixture can be located within the operating arena. The fixture can support the body 102 during the procedure.

The one or more connectors 110, 112 can include features to enable coupling to the fixture. The one or more connectors 110, 112 can be threaded. The one or more connectors 110, 112 can include a serrated plate to limit rotation. The one or more connectors 110, 112 can include any features to ensure a stable connection between the fixture and the body 102. The one or more connectors 110, 112 can be coupled to the body 102. The one or more connectors 110, 112 can include a fastener that secures the one or more connectors 110, 112 to the body.

The one or more connectors 110, 112 can provide redundant fixation options. In some methods, only one connector 110, 112 is used as an attachment point during the surgical procedure. In some methods, two or more connectors 110, 112 are used as attachment points during the procedure.

The blades can move relative to the attachment point of the connector 110, 112. For instance, the blades can slide relative to the attachment point. The attachment point located at the connector 110, 112 can provide stability and accuracy during retraction. The attachment point of the connector 110, 112 can maintain the position of the retractor 100 during the procedure. In some methods, the user does not need to switch between attachment points to allow operation of the blades. Each blade can be manipulated when the body 102 is coupled to the fixture via the connector 110, 112. In some methods, the body 102 is not removed from the fixture during the course of the procedure. In some methods, there is no need to find the surgical site or reposition the retractor after switching attachment points.

The body 102 can include an upper surface 114. The body 102 can include a lower surface 116. The connector 110, 112 can protrude from the upper surface 114. The body 102 can be generally enclosed. The body 102 can include one or more solid surfaces. The body 102 can be low profile. The body 102 can be shaped to minimize obstruction to the surgical site. The body 102 can be at least partially enclosed.

The retractor 100 can include a first blade assembly 120. In some embodiments, the first blade assembly 120 can be an anterior blade assembly. The first blade assembly 120 can include the first blade 122. The first blade 122 can include a first blade proximal end 124. The first blade 122 can include a first blade distal end 126. The first blade 122 can include a first blade longitudinal axis 128. The first blade longitudinal axis 128 can extend from the first blade proximal end 124 to the first blade distal end 126. The first blade longitudinal axis 128 can be perpendicular to the upper surface 114 of the body 102. The first blade longitudinal axis 128 can be perpendicular to the lower surface 116 of the body 102.

The first blade assembly 120 can include a first translation mechanism 130 to translate the first blade 122. The first translation mechanism 130 can include a first rack 132. The first translation mechanism 130 can include a first actuator 134. The first actuator 134 can be disposed within the body 102. The first actuator 134 can be disposed within the first arm 104. The first arm 104 can couple to the first blade assembly 120. The first arm 104 can include a first opening 136. The first rack 132 can extend through the first opening 136. The first rack 132 can extend through the first arm 104 of the body 102. The first rack 132 can move relative to the first actuator 134 to change the position of the first blade 122.

The retractor 100 can include a second blade assembly 140. In some embodiments, the second blade assembly 140 can be a posterior blade assembly. The first blade assembly 120 can be positioned anteriorly relative to the second blade assembly 140 during use. The second blade assembly 140 can be positioned posteriorly relative to the first blade assembly 120 during use. The second blade assembly 140 can include the second blade 142. The second blade 142 can include a second blade proximal end 144. The second blade 142 can include a second blade distal end 146. The second blade 142 can include a second blade longitudinal axis 148. The second blade longitudinal axis 148 can extend from the second blade proximal end 144 to the second blade distal end 146. The second blade longitudinal axis 148 can be perpendicular to the upper surface 114 of the body 102. The second blade longitudinal axis 148 can be perpendicular to the lower surface 116 of the body 102.

The second blade assembly 140 can include a second translation mechanism 150 to translate the second blade 142. The second translation mechanism 150 can include a second rack 152. The second translation mechanism 150 can include a second actuator 154. The second actuator 154 can be disposed within the body 102. The second actuator 154 can be disposed within the second arm 108. The second arm 108 can couple to the second blade assembly 140. The second arm 108 can include a second opening 156. The second rack 152 can extend through the second opening 156. The second rack 152 can extend through the second arm 108 of the body 102. The second rack 152 can move relative to the second actuator 154 to change the position of the second blade 142.

The second blade 142 can include a longitudinally extending slot 160. The longitudinally extending slot 160 can be elongate. The longitudinally extending slot 160 can be rounded. The longitudinally extending slot 160 can be circular or rounded in cross-section. The longitudinally extending slot 160 can be oval in cross-section. The cross-sectional shape of the longitudinally extending slot 160 can include a circle, an oval, a triangle, a rectangle, a square, a polygon, a flattened oval, a thin flattened oval, a rounded rectangle, a thin rounded rectangle, an ellipsoid, or any combination of the foregoing shapes.

The longitudinally extending slot 160 can be partially enclosed. The longitudinally extending slot 160 can be partially enclosed near the second blade proximal end 144. The longitudinally extending slot 160 can be fully enclosed. The longitudinally extending slot 160 can be fully enclosed near the second blade distal end 146. The longitudinally extending slot 160 can form a lumen through the second blade 142. The longitudinally extending slot 160 can extend from the second blade proximal end 144 to the second blade distal end 146.

The second blade 142 can include a channel 162. The channel 162 can extend along the anterior surface of the second blade 142. The channel 162 can extend along the longitudinally extending slot 160. The channel 162 can extend along a portion of the length of the first blade 122. The channel 162 can extend from the first blade proximal end 124. The channel 162 can extend toward the first blade distal end 126. The second blade 142 can engage a probe assembly and shim as described herein.

The first blade 122 can include a width. The width can be transverse to the first longitudinal axis 128. The first blade 122 can include a thickness. The thickness can be transverse to the first longitudinal axis 128. The first blade 122 can include a thickness greater than the width. The first blade 122 can include a major transverse axis along the thickness and a minor transverse axis along the width. The direction of movement can be along the width. The cross-sectional shape of the first blade 122 can include a circle, an oval, a triangle, a rectangle, a square, a polygon, a flattened oval, a thin flattened oval, a rounded rectangle, a thin rounded rectangle, an ellipsoid, or any combination of the foregoing shapes. The first blade 122 can include one or more rounded corners or edges.

The second blade 142 can include a width. The width can be transverse to the second longitudinal axis 148. The second blade 142 can include a thickness. The thickness can be transverse to the second longitudinal axis 148. The second blade 142 can include a thickness greater than the width. The second blade 142 can include a major transverse axis along the thickness and a minor transverse axis along the width. The direction of movement can be along the width. The cross-sectional shape of the second blade 142 can include a concave shape, one or more linear segments, one or more curved segments, one or more chamfered segments, a portion of a polygon, or any combination of the foregoing shapes. The second blade 142 can have a greater thickness than the first blade 122. The second blade 142 can have the same or similar width as the first blade 122. The second blade 142 can include one or more rounded corners or edges.

The first blade 122 can include features to receive one or more tools. The second blade 142 can include features to receive one or more tools. The first blade 122 can include one or more cylindrical channel to receive one or more light sources. The second blade 142 can include one or more cylindrical channel to receive one or more light sources. The first blade 122 can include one or more channels 138. The channel 138 can extend the length of the first blade 122, or a portion thereof. The second blade 142 can include one or more channels 138. The channel 138 can extend the length of the first blade 142, or a portion thereof.

In FIGS. 1-4, the retractor 100 is shown in the closed position. The first blade 122 and the second blade 142 are aligned and relatively close to one another so as to provide a smaller cross-sectional area as compared to one or more opened positions. While the application uses the phrase the closed position, it is understood that one or more positions may be described as closed.

The blades 122, 142 can be aligned, substantially aligned, stacked, substantially stacked, close together, and/or relatively close together. The first blade 122 can at least partially enclose the second blade 142. The first blade 122 can extend along the thickness of the stacked blades. The first blade 122 can have a greater thickness than the second blade 142. The first blade 122 can extend along at least one side of the second blade 142. The first blade 122 can extend along at least two sides of the second blade 142. The first blade 122 can extend along at least three sides of the second blade 142. The first blade 122 can extend along an entire side of the second blade 142. The first blade 122 can extend along a portion of the width of the second blade 142. The first blade 122 can extend along the anterior surface and side surfaces of the second blade 142. The first blade 122 and the second blade 142 can be nested, at least partially nested, substantially nested, abutted, at least partially abutted, substantially abutted, coextensive, at least partially coextensive, substantially coextensive, enclosed, partially enclosed, substantially enclosed, encapsulated, partially encapsulated, substantially encapsulated, set in, partially set in, substantially set in, seated, partially seated, and/or substantially seated. The first blade 122 can at least partially surround, border, bound, circumscribe, confine, encompass, box in, form a perimeter around, and/or encircle the second blade 142. The first blade 122 can at least partially enclose the second blade 142. The second blade 142 can be inserted into a space of the first blade 122. The first blade 122 and the second blade 142 can be substantially parallel or parallel in the closed position. The longitudinal axes 128, 148 of the first blade 122 and the second blade 142 can be aligned on substantially the same or the same plane in the closed position. The length of the blades 122, 142 can be approximately equal to the length of one blade, such as the length of the first blade 122. The first blade 122 and the second blade 142 can have a stacked configuration. The first blade 122 can be along a first side and the second blade 142 can be along a second side. The first blade 122 can be anterior and the second blade 142 can be posterior. The first blade 122 can be closer to the first arm 104 and the second blade 142 can be closer to the second arm 108. Other embodiments are contemplated. For instance, the first blade 122 and the second blade 142 can be reversed relative to the body. The first blade assembly 120 can couple to the second arm 108 and the second blade assembly 140 can couple to the first arm.

The retractor 100 can be generally symmetrical. The first rack 132 can align or generally align with the second rack 152. The first rack 132 and the second rack 152 can be coaxial. The first opening 136 can align or generally align with the second opening 156. The first opening 136 and the second opening 156 can be coaxial. The first arm 104 can align or generally align with the second arm 108. The first arm 104 and the second arm 108 can be parallel.

The first blade assembly 120 and the second blade assembly 140 can have the same or similar features. The first rack 132 and the second rack 152 can be identical. The first rack 132 and the second rack 152 can be the mirror image of each other. The first rack 132 and the second rack 152 can be diametrically opposed. The first blade assembly 120 can have gears on an inner surface. The second blade assembly 140 can have gears on an outer surface. The first blade assembly 120 and the second blade assembly 140 can have gears on opposite surfaces.

The first actuator 134 and the second actuator 154 can be identical. The first actuator 134 and the second actuator 154 can have the same number of gears. The first actuator 134 and the second actuator 154 can have the same diameter. The first actuator 134 and the second actuator 154 can be pinions. The first actuator 134 and the second actuator 154 can be the mirror image of each other. The first actuator 134 and the second actuator 154 can be configured to be rotated in the same direction to open the retractor 100. In the illustrated embodiment, the first actuator 134 can be rotated clockwise to open the retractor 100. In the illustrated embodiment, the second actuator 154 can be rotated clockwise to open the retractor 100. In some embodiments, the first actuator 134 can be rotated counter-clockwise to open the retractor 100. In some embodiments, the second actuator 154 can be rotated counter-clockwise to open the retractor 100. In other embodiments, the first actuator 134 and the second actuator 154 can be configured to be rotated in the opposite direction to open the retractor 100. In some embodiments, the first actuator 134 and the second actuator 154 can be offset. The first actuator 134 can be closer to the central portion 106. The second actuator 154 can be farther from the central portion 106. In some embodiments, the first actuator 134 and the second actuator 154 are coaxial.

Figure 7:
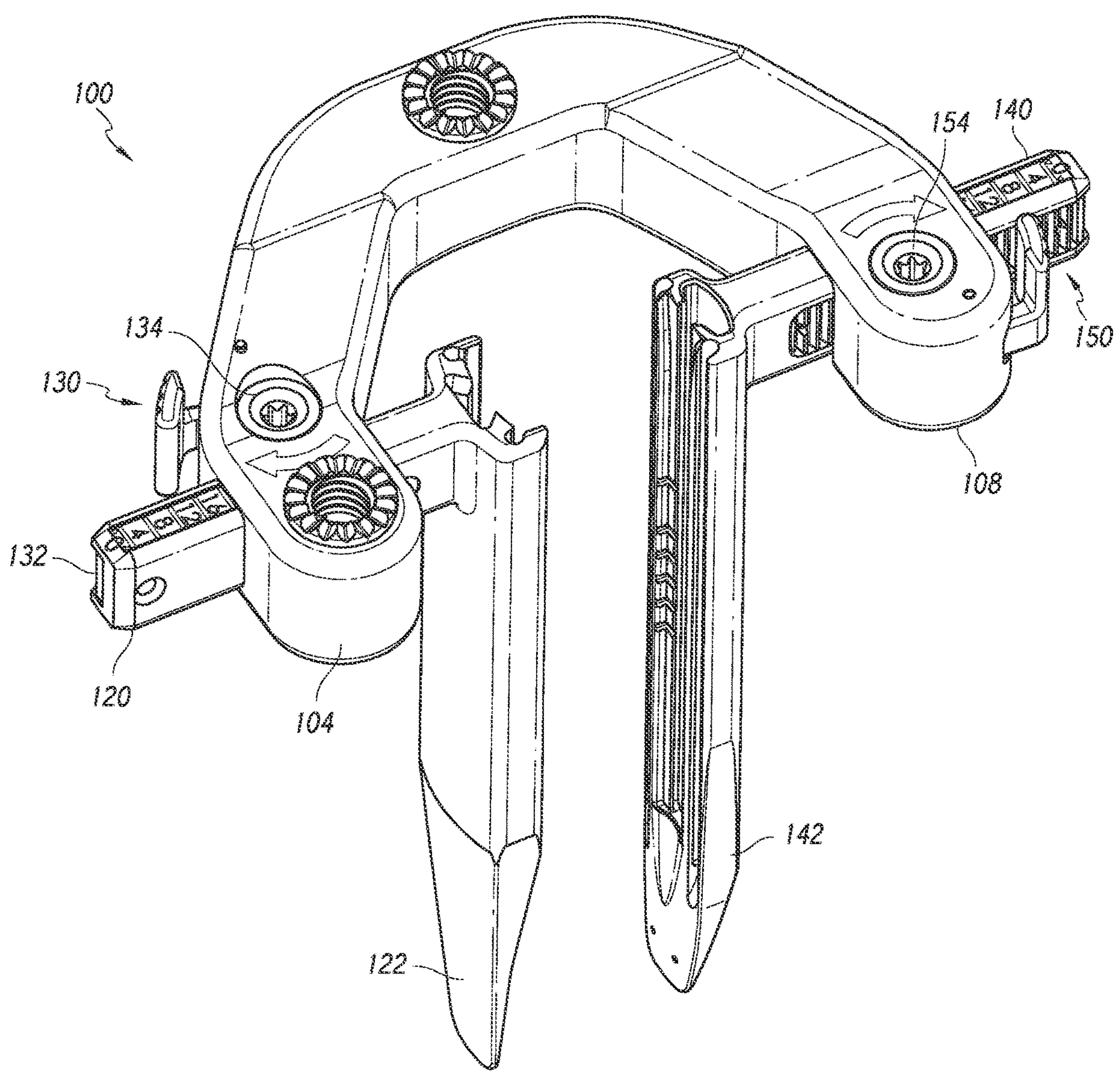
FIG. 7 provides a perspective view of an embodiment of the retractor of FIG. 1 with the blades in an opened position.
Figure 8:
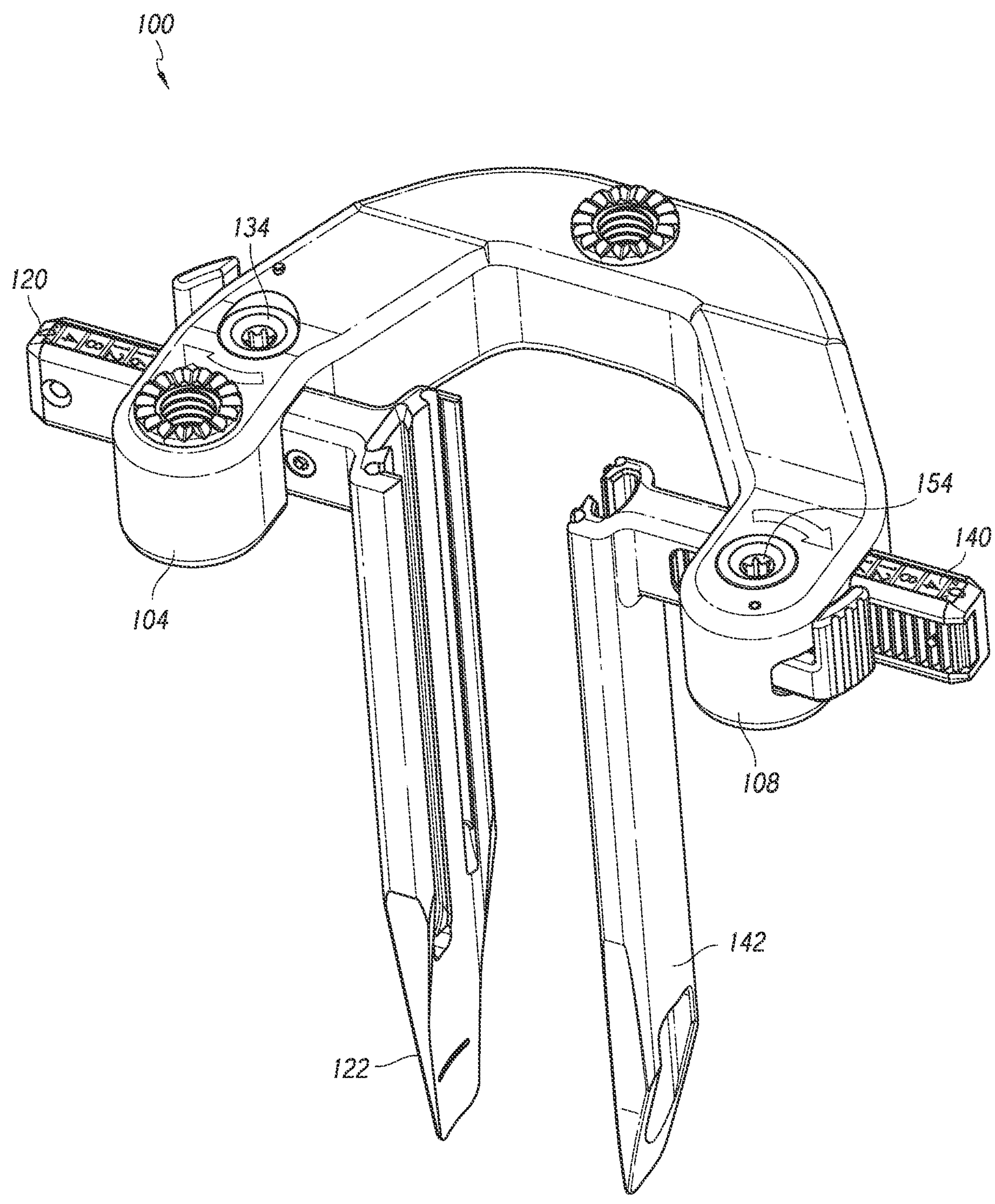
FIG. 8 provides another perspective view of the retractor of FIG. 7 with the blades in an opened position.
Figure 9:
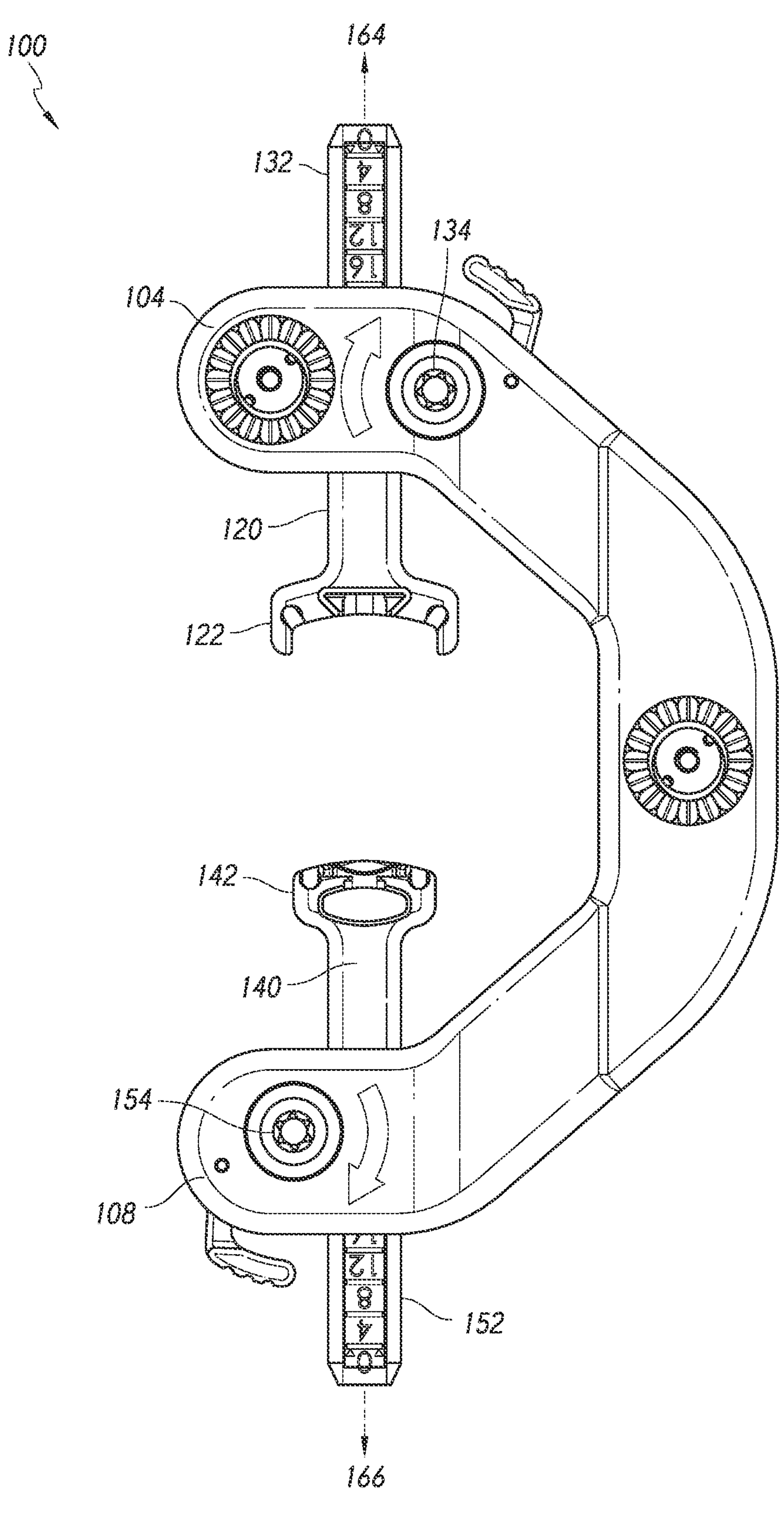
FIG. 9 provides a top view of the retractor of FIG. 7 with the blades in an opened position.
Figure 10:
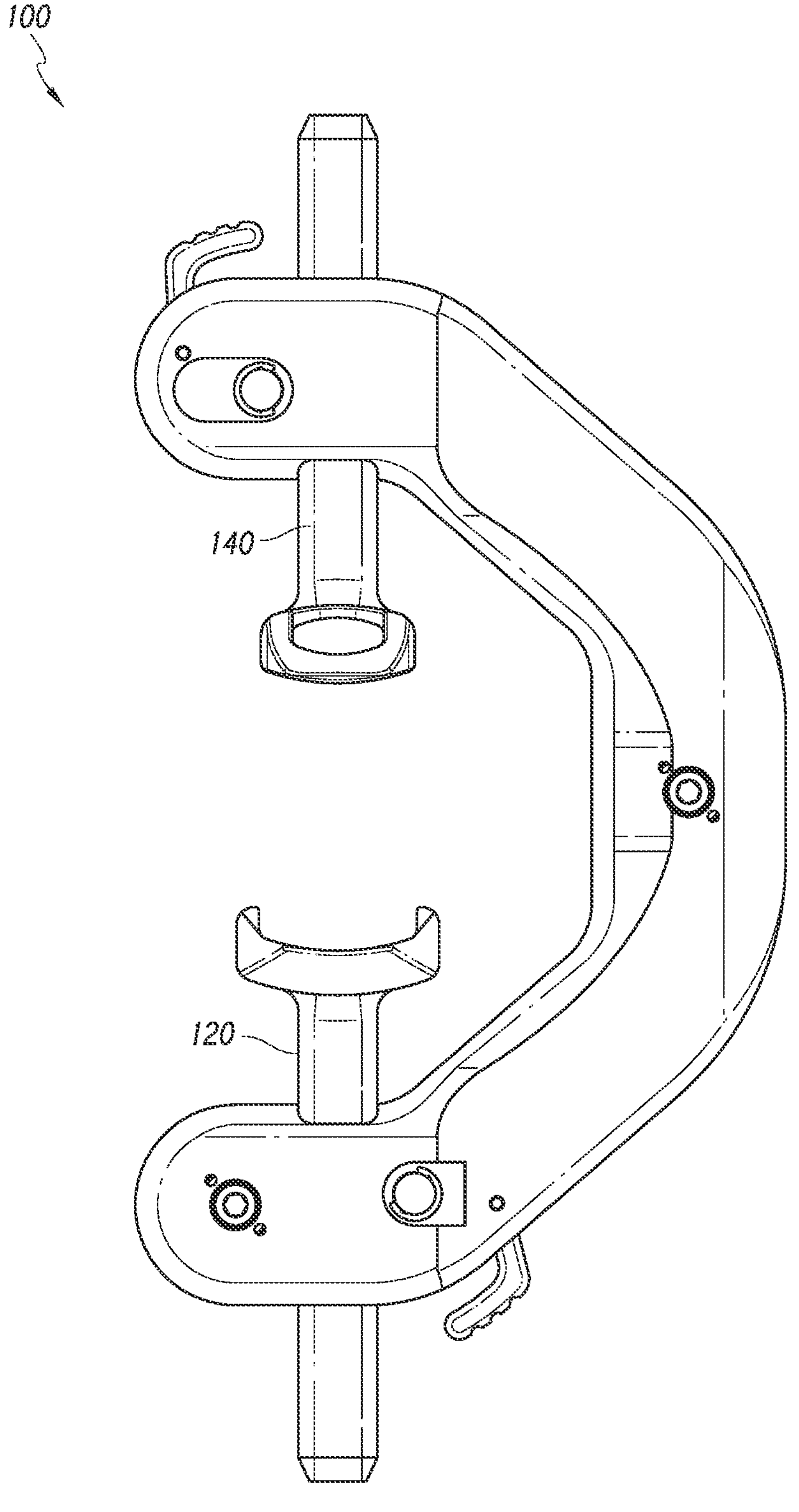
FIG. 10 provides a bottom view of the retractor of FIG. 7 with the blades in an opened position.
Figure 11:
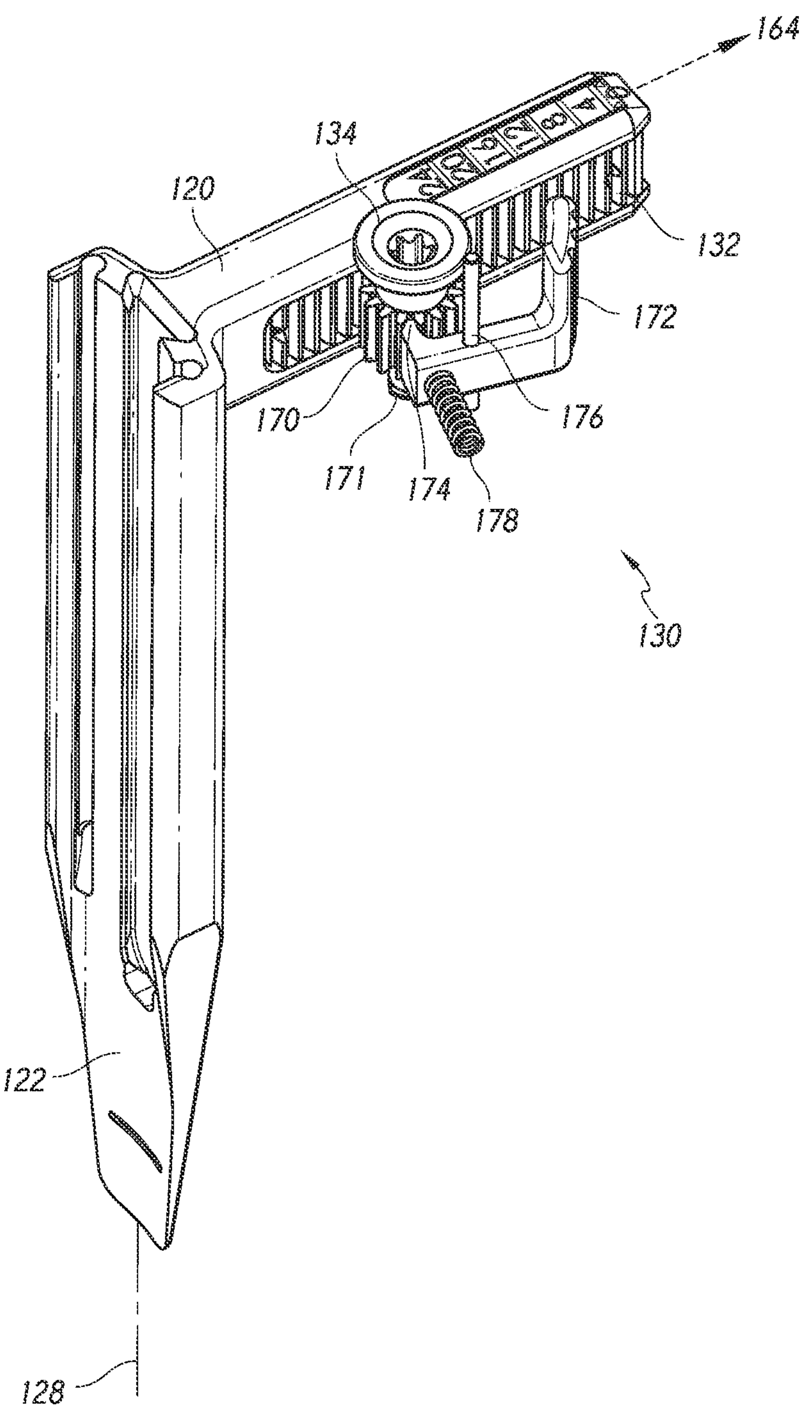
FIG. 11 provides a perspective view of a mechanism of the retractor of FIG. 1.
Figure 12:
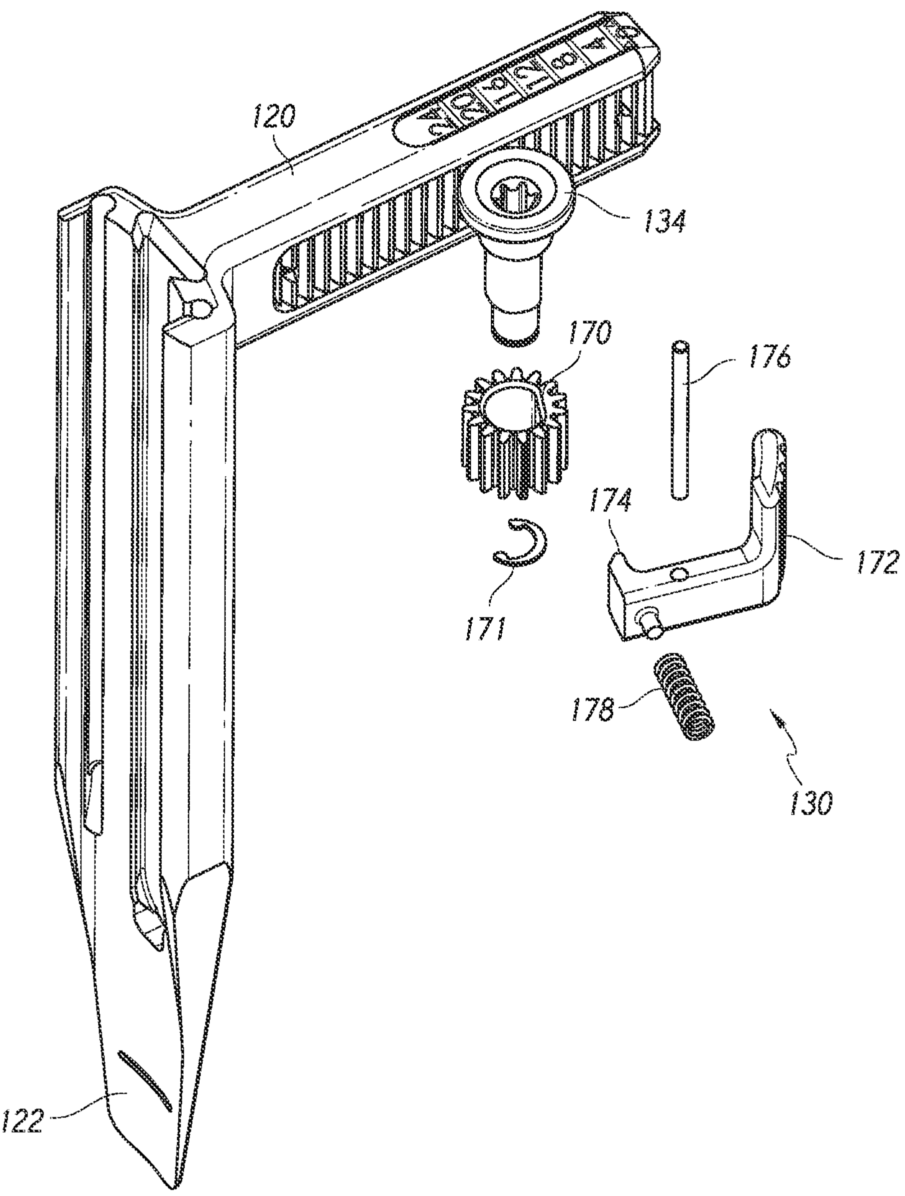
FIG. 12 provides an exploded view of the mechanism of the retractor of FIG. 11.
Figure 13:
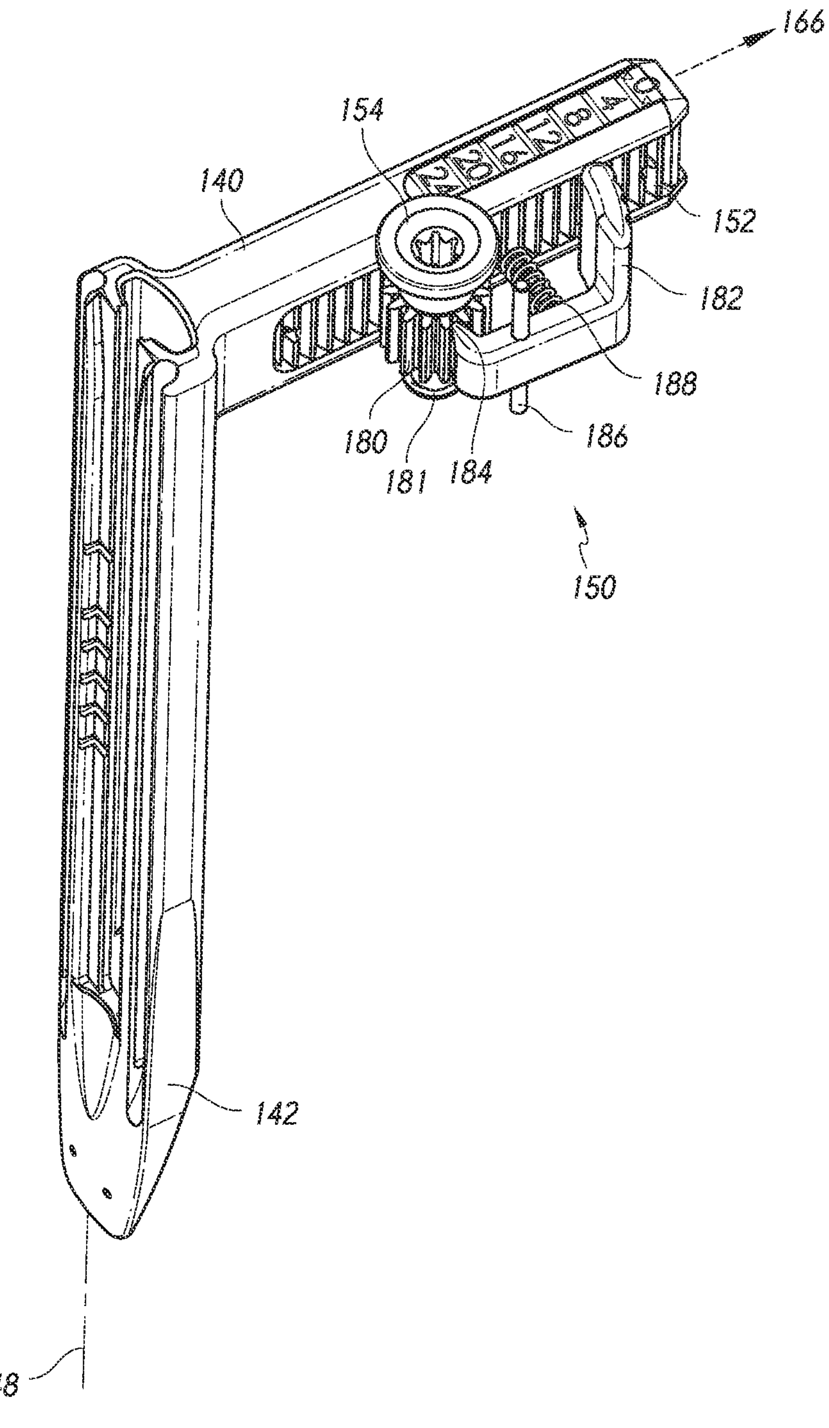
FIG. 13 provides a perspective view of a mechanism of the retractor of FIG. 1.
Figure 14:
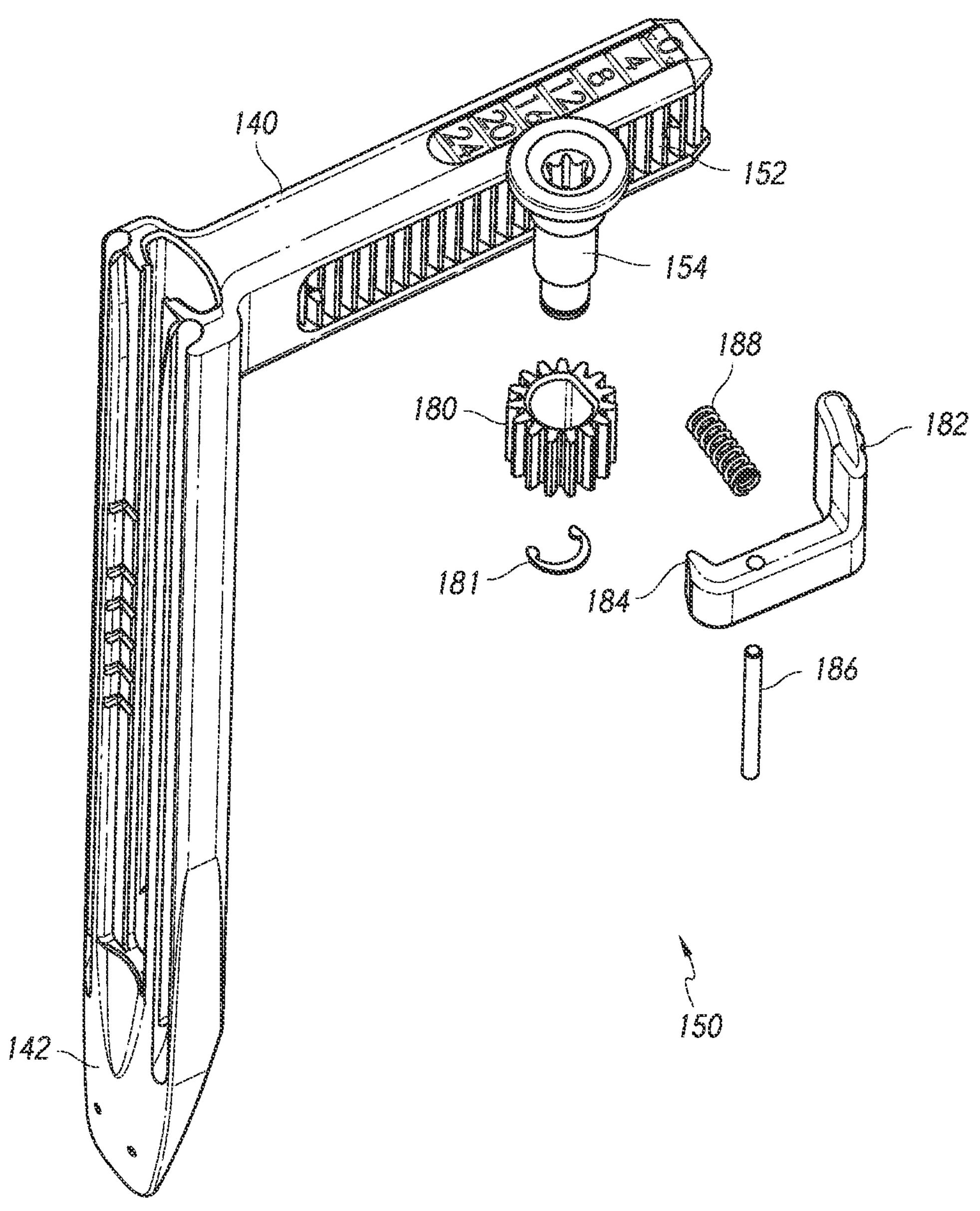
FIG. 14 provides an exploded view of the mechanism of the retractor of FIG. 13.

FIG. 7 provides a perspective view of the retractor 100 with the blades in an opened position. FIG. 8 provides another perspective view of the retractor 100 with the blades in an opened position. FIG. 9 provides a top view of the retractor of 100 with the blades in an opened position. FIG. 10 provides a bottom view of the retractor 100 with the blades in an opened position. FIG. 11 provides a perspective view of the translation mechanism 130. FIG. 12 provides an exploded view of the translation mechanism 130. FIG. 13 provides a perspective view of the translation mechanism 150. FIG. 14 provides an exploded view of the translation mechanism 150.

The first actuator 134 and the second actuator 154 can be separately rotatable. The user can rotate the first actuator 134 to open the first blade assembly 120. The user can rotate the first actuator 134 to move the first blade 122 toward the first arm 104. The user can rotate the second actuator 154 to open the second blade assembly 140. The user can rotate the second actuator 154 to move the second blade 142 toward the second arm 108. The first actuator 134 and the second actuator 154 can be rotated to different degrees. The first actuator 134 and the second actuator 154 can be rotated at different times. The first actuator 134 and the second actuator 154 can be rotated together. The first actuator 134 and the second actuator 154 can be rotated simultaneously. The first actuator 134 and the second actuator 154 can be rotated independently.

The first translation mechanism 130 can translate the first blade 122 along a first translation direction 164. The second translation mechanism 150 can translate the second blade 142 along a second translation direction 166. The first translation direction 164 and the second translation direction 166 can be along the same axis. The first translation direction 164 and the second translation direction 166 can be opposite directions. The first translation direction 164 can extend along the first rack 132. The first translation direction 164 can open the first blade 122. The second translation direction 166 can extend along the second rack 152. The second translation direction 166 can open the second blade 142. In some embodiments, the retractor 100 can include linear translation. The translation can follow a straight line. The translation can follow two straight lines. In other embodiments, the retractor 100 can include non-linear or curved translation. The translation can follow an arc. The translation can follow a continuous arc. The first translation mechanism 130 and the second translation mechanism 150 can translate the blades 122, 142 in opposite directions. The first translation mechanism 130 and the second translation mechanism 150 can open the blades 122, 142.

FIGS. 11-12 illustrate the first translation mechanism 130 of the retractor 100. The first translation mechanism 130 can include the first rack 132. In some embodiments, the first rack 132 and the first blade 122 are integrally formed. In some embodiments, the first rack 132 and the first blade 122 are separately formed. The first rack 132 and the first blade 122 can be coupled by one or more fasteners.

The first translation mechanism 130 can include the first actuator 134. The first translation mechanism 130 can be a rack and pinon mechanism. The first actuator 134 can include first gears 170. The first gears 170 can be shaped and sized to engage the first rack 132. The first actuator 134 can include pinion gears. The first rack 132 can include linear gears. The first translation mechanism 130 can convert rotational motion of the first actuator 134 into linear motion of the first rack 132. The relative motion between the first rack 132 and the first actuator 134 can be determined by the gear size of the first gears 170 of the first actuator 134. The first gears 170 can be retained relative to the actuator 134 by a clip 171.

The first actuator 134 can be rotated to open the first blade 122. The first actuator 134 can be freely rotated to open the retractor 100. The retractor 100 can include features to prevent rotation of the first actuator 134. The retractor 100 can include a lock. The retractor 100 can limit or prevent closing of the blades.

The retractor 100 can include a first lock handle 172. The first lock handle 172 can include a finger grip. The lock handle 172 can be depressed by the user. The first lock handle 172 can be depressed to pivot the first lock handle 172. The first lock handle 172 can be depressed to be unlocked. The first lock handle 172 can be depressed to allow the closing of the first blade 122. The first lock handle 172 can be released to lock. The first lock handle 172 can be released to prevent or limit the closing of the first blade 122.

The first lock handle 172 can include a first pawl 174. The first pawl 174 can be configured to engage a gear of the first actuator 134. The first pawl 174 can be configured to disengage the first actuator 134 when the first lock handle 172 is depressed. The first pawl 174 can be configured to engage the first actuator 134 when the first lock handle 172 is released.

The retractor 100 can include a first pivot pin 176. The first lock handle 172 can pivot relative to the first pivot pin 176. The first lock handle 172 can pivot when the user depresses the first lock handle 172. The first lock handle 172 can pivot the first pawl 174 into engagement and out of engagement with the first actuator 134. The retractor 100 can include a first spring 178. The first spring 178 can bias the first pawl 174 into engagement with the first actuator 134. The user can overcome the biasing force of the first spring 178 by depressing the first lock handle 172.

In some embodiments, the first pawl 174 engages the first actuator 134 in a neutral configuration. The first spring 178 biases the first pawl 174 into engagement. The first pawl 174 can allow rotation in one direction. The first pawl 174 can allow the first blade 122 to open. The first pawl 174 can limit or prevent rotation of the actuator 134 in another, opposite direction. The first pawl 174 can prevent or limit the first blade 122 from closing. In some embodiments, the first lock handle 172 is locked in the neutral configuration.

In some embodiments, the first lock handle 172 is depressed by the user. The first pawl 174 pivots out of engagement with the first actuator 134. The first pawl 174 pivots relative to the first pivot pin 176. The first spring 178 is compressed. The first actuator 134 can be freely rotated without interference with the first pawl 174. The user can manually close the first blade 122. The first blade 122 can be moved toward the second arm 108. The first blade 122 can be freely slid by the user. The first pawl 174 can be disengaged from the first actuator 134 when the first lock handle 172 is depressed. The first actuator 134 can freely spin as the first rack 132 is moved. In some embodiments, the first lock handle 172 must be depressed to close the first blade 122. In some embodiments, the retractor 100 requires an active close. In some embodiments, the first actuator 134 is rotated to open the first blade 122. In some embodiments, the first actuator 134 is prevented from being rotated to close the first blade 122. In some embodiments, the first actuator 134 cannot close the first blade 122 due to the engagement of the first pawl 174 with the first actuator 134. The pawl 174 can prevent or limit rotation of the first actuator 134 in a direction to close the first blade 122. In some embodiments, the retractor 100 requires an extra step of depressing the first lock handle 172 to collapse the first blade 122. In some embodiments, the retractor 100 requires depressing the first lock handle 172 and actuating the first actuator 134 to collapse the first blade 122. In some embodiments, the first lock handle 172 can be released when the first blade 122 is closed. The first spring 178 biases the first pawl 174 into engagement with the first actuator 134.

FIGS. 13-14 illustrates the second translation mechanism 150 of the retractor 100. The second translation mechanism 150 can have the same or similar features as the first translation mechanism 130. The second translation mechanism 150 can include the second rack 152. In some embodiments, the second rack 152 and the second blade 142 are integrally formed. In some embodiments, the second rack 152 and the second blade 142 are separately formed. The second rack 152 and the second blade 142 can be coupled by one or more fasteners.

The second translation mechanism 150 can include the second actuator 154. The second translation mechanism 150 can be a rack and pinon mechanism. The second actuator 154 can include second gears 180. The second gears 180 can be shaped and sized to engage the second rack 152. The second actuator 154 can include pinion gears. The second rack 152 can include linear gears. The second translation mechanism 150 can convert rotational motion of the second actuator 154 into linear motion of the second rack 152. The relative motion between the second rack 152 and the second actuator 154 can be determined by the gear size of the second gears 180 of the second actuator 154. The second gears 180 can be retained relative to the actuator 154 by a clip 181.

The second actuator 154 can be rotated to open the second blade 142. The second actuator 154 can be freely rotated in one direction to open the retractor 100. The retractor 100 can include features to prevent rotation of the second actuator 154 in an opposite direction. The retractor 100 can include a lock. The retractor 100 can limit or prevent closing of the blades.

The retractor 100 can include a second lock handle 182. The second lock handle 182 can include a finger grip. The second lock handle 182 can be depressed by the user. The second lock handle 182 can be depressed to pivot the second lock handle 182. The second lock handle 182 can be depressed to be unlocked. The second lock handle 182 can be depressed to allow the closing of the second blade 142. The second lock handle 182 can be released to lock. The second lock handle 182 can be released to prevent or limit the closing of the second blade 142.

The second lock handle 182 can include a second pawl 184. The second pawl 184 can be configured to engage a gear of the second actuator 154. The second pawl 184 can be configured to disengage the second actuator 154 when the second lock handle 182 is depressed. The second pawl 184 can be configured to engage the second actuator 154 when the second lock handle 182 is released. In some embodiments, the retractor 100 requires depressing the second lock handle 182 and actuating the second actuator 154 to collapse the second blade 142.

The retractor 100 can include a second pivot pin 186. The second lock handle 182 can pivot relative to the second pivot pin 186. The second lock handle 182 can pivot when the user depresses the second lock handle 182. The second lock handle 182 can pivot the second pawl 184 into engagement and out of engagement with the second actuator 154. The retractor 100 can include a second spring 188. The second spring 188 can bias the second pawl 184 into engagement with the second actuator 154. The user can overcome the biasing force of the second spring 188 by depressing the second lock handle 182.

In some embodiments, the second pawl 184 engages the second actuator 154 in a neutral configuration. The second spring 188 biases the second pawl 184 into engagement. The second pawl 184 can limit or prevent rotation of the second actuator 154 in one direction. The second pawl 184 can allow the second blade 142 to open. The second pawl 184 can prevent or limit the second blade 142 from closing. In some embodiments, the second lock handle 182 is locked in the neutral configuration.

In some embodiments, the second lock handle 182 is depressed by the user. The second pawl 184 pivots out of engagement with the second actuator 154. The second pawl 184 pivots relative to the second pivot pin 186. The second spring 188 is compressed. The second actuator 154 can be freely rotated without interference with the second pawl 184. The user can manually close the second blade 142. The second blade 142 can be moved toward the first arm 104. The second blade 142 can be freely slid by the user. The second pawl 184 is disengaged from the second actuator 154. The second actuator 154 freely spins as the second rack 152 is moved. In some embodiments, the second lock handle 182 must be depressed to close the second blade 142. In some embodiments, the retractor 100 requires an active close. In some embodiments, the second actuator 154 is rotated to open. In some embodiments, the retractor 100 requires an extra step of depressing the second lock handle 182 to collapse. The second lock handle 182 can be released when the second blade 142 is closed. The second spring 188 biases the second pawl 184 into engagement with the second actuator 154 when the second lock handle 182 is released.

The first translation mechanism 130 translates the first blade 122 about the first translation direction 164 to open the first blade 122. In the illustrated arrangement, the first translation direction 164 intersects the longitudinal axis 128 of the first blade 122. The first translation direction 164 can be perpendicular to the longitudinal axis 128 of the first blade 122. The first blade 122 translates in a direction perpendicular or generally perpendicular to the longitudinal axis 128 of the first blade 122. The first blade 122 can be substantially vertical. The first translation direction 164 can be substantially horizontal.

The second translation mechanism 150 translates the second blade 142 about the second translation direction 166 to open the second blade 142. In the illustrated arrangement, the second translation direction 166 intersects the longitudinal axis 148 of the second blade 142. The second translation direction 166 can be perpendicular to the longitudinal axis 148 of the second blade 142. The second blade 142 translates in a direction perpendicular or generally perpendicular to the longitudinal axis 148 of the second blade 142. The second blade 142 can be substantially vertical. The second translation direction 166 can be substantially horizontal.

In some embodiments, the longitudinal axes 128, 148 of the blades 122, 142 may be substantially coplanar with one another. In some embodiments, the longitudinal axes 128, 148 of the blades 122, 142 can be substantially parallel to one another. The longitudinal axes 128, 148 of the blades 122, 142 can remain coplanar or parallel during translational movement. In some embodiments, the translation directions 164, 166 may be substantially coaxial with one another. In some embodiments, the translation directions 164, 166 can be substantially parallel to one another. The translation directions 164, 166 can remain coplanar, parallel, or coaxial during translational movement. In some embodiments, the translation directions 164, 166 are at some pre-determined skew angle with respect to one another. In some embodiments, the translation directions 164, 166 are offset with respect to one another. In some embodiments, "substantially" can mean within plus or minus 25 degrees from the given orientation, in other embodiments, within plus or minus 10 degrees from the given orientation, and in other embodiments, within plus or minus 5 degrees from the given orientation.

In some embodiments, one or more blade assemblies can engage the retractor 100. The blade assemblies can have blades of different lengths. The blade assemblies can have blades of different widths. The blade assemblies can have blades of different thicknesses. The blade assemblies can have blades of different shapes. The blade assemblies can have blades of different configurations. One or more blade assemblies can have the first rack 132. One or more blade assemblies can have the second rack 152.

In the illustrated embodiment, components of the first blade assembly 120 translate as a unit. The first blade assembly 120 can include the first blade 122 and the first rack 132. The first blade 122 and the first rack 132 can be coupled together. In some embodiments, the first blade 122 and the first rack 132 can be integrally formed or monolithically formed. The first blade 122 and the first rack 132 can translate relative to the first actuator 134 when the first actuator 134 is rotated. The first rack 132 can extend through the first opening 136 to allow the first rack 132 to engage the first gears 170 and the first actuator 134.

In the illustrated embodiment, components of the second blade assembly 140 translate as a unit. The second blade assembly 140 can include the second blade 142 and the second rack 152. The second blade 142 and the second rack 152 can be coupled together. In some embodiments, the second blade 142 and the second rack 152 can be integrally formed or monolithically formed. The second blade 142 and the second rack 152 can translate relative to the second actuator 154 when the second actuator 154 is rotated. The second rack 152 can extend through the second opening 156 to allow the second rack 152 to engage the second gears 180 and the second actuator 154.

The first blade assembly 120 and second blade assembly 140 can allow the blades 122, 142 to spread. The actuators 134, 154 can be rotated to spread the first blade 122 and the second blade 142 relative to the body 102. In the illustrated embodiment, the first blade 122 and the second blade 142 can move relative to one another along a straight line. In the illustrated embodiment, the general direction of motion of the first blade 122 and the second blade 142 relative to one another can be along a common axis. In some embodiments, the translation directions 164, 166 can be along a common axis. In other embodiments, the general direction of motion of the first blade 122 and the second blade 142 relative to one another can be about different axes (e.g., axes that are parallel to each other or slightly skewed).

In some embodiments, the retractor 100 described herein possesses a mechanism for locking the first blade assembly 120 and the second blade assembly 140 to prevent or limit closing of the first blade 122 and the second blade 142. The retractor 100 can include the lock handle 172, 182. The lock handle 172, 182 can be pivoted to disengage the pawl 174, 184 from the actuator 134, 154. The lock handle 172, 182 can be released to bias the pawl 174, 184 into engagement with the actuator 134, 154. The pawl 174, 184 can function to limit rotation of the actuator 134, 154 in one direction. The pawl 174, 184 can function to limit rotation of the actuator 134, 154 to close the retractor 100.

The first blade 122 can translate independently of the second blade 142. The second blade 142 can translate independently of the first blade 122. The first blade 122 and the second blade 142 can translate simultaneously. The first blade 122 and the second blade 142 can translate sequentially. The first blade 122 can translate along a portion of the distance between the first arm 104 and the second arm 108 of the body 102. The first blade 122 can translate along a percentage of the distance between the first arm 104 and the second arm 108 including 10%, 20%, 20%, 30%, 40%, 50%, 60%, 70%, 80%, 90%, 100%, or any range of two of the foregoing values. The first blade 122 can translate the distance of the corresponding gears of the first rack 132. The second blade 142 can translate along a portion of the distance between the first arm 104 and the second arm 108 of the body 102. The second blade 142 can translate along a percentage of the distance between the first arm 104 and the second arm 108 including 10%, 20%, 20%, 30%, 40%, 50%, 60%, 70%, 80%, 90%, 100%, or any range of two of the foregoing values. The second blade 142 can translate the distance of the corresponding gears of the second rack 152.

The first actuator 134 can be actuated independently of the second actuator 154. The second actuator 154 can be actuated independently of the first actuator 134. The first actuator 134 and the second actuator 154 can be actuated simultaneously. The first actuator 134 and the second actuator 154 can be actuated sequentially. In some methods, the first actuator 134 and the second actuator 154 can move together to spread the blades 122, 142. In some embodiments, the first blade 122 can remain stationary as the second blade 142 translates. In some embodiments, the second blade 142 can remain stationary as the first blade 122 translates.

The blades 122, 142 may have a variety of configurations. The blades 122, 142 can be flattened to facilitate the stacked configuration. The blades 122, 142 can have a complementary shape. The blades 122, 142 can have an interlocking shape. In some embodiments, at least a portion of the second blade 142 can nest within a portion of the first blade 122. The blades 122, 142 can have a nested shape. The blades 122, 142 can have a low-profile shape. The blades 122, 142 can form smooth edges. The blades 122, 142 can form rounded edges. In some embodiments, at least one blade is substantially flat. In some embodiments, at least one blade is bent or beveled in order to enhance the ability of the blades to lie flat when the blades are in the closed position. The closed position can allow the first and second blades 122, 142 to exert force on the skin about an incision in opposing directions. The closed position can allow the first and second blades 122, 142 to exert force on the skin about an incision substantially perpendicular to the longitudinal axes 128, 148. The closed position can allow the first and second blades 122, 142 to exert force on the skin about an incision to widen the incision. The closed position can allow the first and second blades 122, 142 to exert force on the skin about an incision to enlarge the incision in a single direction of movement. The closed position can allow the first and second blades 122, 142 to exert force on the skin about an incision to widen the incision without lengthening the incision.

In some embodiments, the blades 122, 142 are of substantially different sizes in at least one dimension. In some embodiments, the blades 122, 142 have different lengths. In some embodiments, the blades 122, 142 have different widths. In some embodiments, the blades 122, 142 have different thicknesses. In some embodiments, the blades 122, 142 have different configurations. In some embodiments, the blades 122, 142 have the same length. In some embodiments, the blades 122, 142 have the same width. In some embodiments, the blades 122, 142 have the same thickness. In some embodiments, at least one of the blades 122, 142 is a substantially flat blade. In some embodiments, at least one of the blades 122, 142 is a substantially concave blade. In some embodiments, the blades 122, 142 are removable. In some embodiments, the blade assemblies 120, 140 are removable from the retractor body 102.

In some embodiments, the blades 122, 142 can be removed from the blade assemblies 120, 140. In some embodiments, the racks 132, 152 can be removed from the blade assemblies 120, 140. In some arrangement, the blade assemblies 120, 140 can be removed from the body 102. The racks 132, 152 can slide through the openings 136, 156 in the body 102 to allow the blade assemblies 120, 140 to be removed. In some arrangement, it can be convenient to remove the blade assemblies 120, 140 in order to expedite sterilization of the blade assemblies 120, 140. In some arrangement, it can be convenient to remove the blade assemblies 120, 140 in order to exchange one or both blade assemblies 120, 140 for other blade assemblies 120, 140 such as assemblies with different size blades or different configuration of blades.

In FIGS. 1-4, the retractor 100 is shown in the "closed position," meaning that the first blade 122 and the second blade 142 are aligned and relatively close to one another so as to provide a smaller cross-sectional area as compared to an "opened position". While the application uses the phrase "the closed position," it is understood that one or more positions may be described as closed. For instance, the blades 122, 142 may be aligned, substantially aligned, stacked, substantially stacked, close together, relatively close together, the first blade 122 encloses the second blade 142, the second blade 142 encloses the first blade 122, the first blade 122 encloses the probe assembly 200, the second blade 142 encloses the probe assembly 200, or any other closed positions.

The first blade 122 and the second blade 142 can be substantially parallel or parallel in the closed position. The first blade distal end 126 and the second blade distal end 146 can align. The first blade 122 and the second blade 142 can have the same length. The first blade 122 and the second blade 142 can generally taper toward the distal end. The first blade 122 and the second blade 142 can have the same taper. The first blade 122 and the second blade 142 can have different tapers. The first blade 122 can be centered relative to the second blade 142. The second blade 142 can be centered relative to the first blade 122. The first blade 122 can extend along both sides of the second blade 142, or a portion of the sides thereof. The second blade 142 can at least partially extend into the first blade 122. The first blade 122 can extend along at least a portion of the width of the second blade 142.

The longitudinal axes 128, 148 of the first blade 122 and the second blade 142 can be aligned on substantially the same or the same plane in the closed position. The length of the blades 122, 142 in this configuration can be approximately equal to the length of one blade, such as the length of the first blade 122. The thickness of the blades 122, 142 in this configuration can be approximately equal to the length of one blade, such as the thickness of the first blade 122. The width of the blades 122, 142 in this configuration can be greater than the width of one blade but less than the total width of each blade separately. The width of the blades 122, 142 in this configuration is greater than the width of the first blade 122. The width of the blades 122, 142 in this configuration is greater than the width of the second blade 142. The width of the blades 122, 142 in this configuration is less than the addition of the separate width of the first blade 122 and the separate width of the second blade 142. The first blade 122 and the second blade 142 can have a nested configuration which reduces the total width of the blades 122, 142 in the closed configuration. The first blade 122 can be to the anterior side and the second blade 142 can be to the posterior side. The first blade 122 can have a concave shape. The second blade 142 can have a convex shape. The first blade 122 can form rails that align the sides of the second blade 142. The first blade 122 and the second blade 142 can have an overlapped configuration in the closed position.

In FIGS. 7-10, the retractor 100 is shown in an "opened position," meaning that the first blade 122 can be translated relative to the second blade 142, or the second blade 142 can be translated relative to the first blade 122, or both the first blade 122 and the second blade 142 can be translated. The first blade 122 and the second blade 142 can be moved apart from their initial closed position. While the application uses the phrase "the opened position," it is understood that one or more positions may be described as opened. For instance, one or more of the blades 122, 142 may be slightly spaced apart, greatly spaced apart, overlapping, not overlapping, adjacent, with a gap between, without a gap between, at any spaced apart location along the translation directions 164, 166, wherein the total width in the opened position is greater than the incision width, wherein the total width in the opened position is greater than the width in the closed position, or wherein width of the blades 122, 142 in the opened position is greater than the width of both blades.

In some embodiments, the motion of the first blade 122 can be decoupled from the motion of the second blade 144 such that each actuator 134, 154 is separately actuated. In some embodiments, the motion of the first blade 122 can be coupled to the motion of the second blade 144 such that actuation moves both the first blade 122 and the second blade 142. The first blade 122 and the second blade 142 can be positioned to allow translation from the initial position without interference in one direction, to spread the blades 122, 142. In some embodiments, the blades 122, 142 can form the closed position at a midpoint between the first arm 104 and the second arm 108. In some embodiments, the blades 122, 142 can form the closed position at a point offset from the midpoint between the first arm 104 and the second arm 108. The blades 122, 142 can form the closed position at any position between the first arm 104 and the second arm 108.

The first blade 122 can translate a first distance toward the first arm 104. The second blade 142 can translate a second distance toward the second arm 108. The first distance can be equal to the second distance. The first distance can be not equal to the second distance. The configuration of the blades 122, 142 permits the blades 122, 142 to translate toward the respective arms 104, 108 to open without interference of the other blade 122, 142.

The retractor 100 can include the actuator 134, 154. The actuator 134, 154 interacts with the racks 132, 152 to spread the blades 122, 142. The first actuator 134 can be rotated clockwise to move the first blade 122 toward the first arm 104. The second actuator 154 can be rotated clockwise to move the second blade 142 toward the second arm 108.

Rotation of the actuator 134, 154 results in the racks 132, 154 and therefore the blades 122, 142 moving apart along the translation directions 164, 166 causing retractor 100 to assume the opened position. In the illustrated embodiment, the translation directions 164, 166 form a line. The blade assemblies 120, 140 convert rotational movement of the actuators 134, 154 to linear motion of the racks 132, 154 and blades 122, 142. The first blade 122 follows a linear path toward the first arm 104. The second blade 142 follows a linear path toward the second arm 108.

Inserting the blades 122, 142 into an incision in the closed position and translating at least one of the first blade 122 and the second blade 142 to an opened position results in a stretching of the incision along at least one translation direction 164, 166. This stretching increases the width of the incision from a length approximately equal to the width of the nested blades 122, 142 to a greater width. As can be seen in FIGS. 7-10, the retractor 100 is in the opened position, meaning that the first blade 122 is relatively separated from the second blade 142.

The components of the first blade assembly 120 can be substantially similar to the embodiment of the components of the second blade assembly 140. The first rack 132 and the second rack 152 can be the same or similar. The first actuator 134 and the second actuator 154 can be the same or similar. The first gears 170 and the second gears 180 can be the same or similar. The first lock handle 172 and the second lock handle 182 can be the same or similar. The function of the translation of the first blade assembly 120 and the second blade assembly 140 can be the same or substantially similar.

Some embodiments contemplate kits comprising the retractor 100. In some embodiments, the kit comprises a plurality of removable and exchangeable blade assemblies 120, 140. In some embodiments, the kit comprises a plurality of removable and exchangeable blades 122, 142. In some embodiments, the kit comprises a plurality of removable and exchangeable racks 132, 152 and corresponding gears 170, 180 and actuators 134, 154. In some embodiments, a kit is provided comprising one or more racks 132, 152 and corresponding gears 170, 180. In some embodiments, the racks 132, 152 and gears 170, 180 are removable and exchangeable. In some embodiments, the kit comprises a plurality of bodies 102. Each kit may comprise different translation mechanisms. Each kit may comprise the same translation mechanism among different blade assemblies. In some embodiments, the kit comprises at least two blade assemblies having amongst the two blade assemblies at least two distinct blade configurations. In other embodiments, the kit comprises one blade assembly, two blade assemblies, three blade assemblies, four blade assemblies, five blade assemblies, six blade assemblies, seven blade assemblies, eight blade assemblies, or any range of the foregoing values, having amongst the several blade assemblies from one distinct blade configuration, two distinct blade configurations, three distinct blade configurations, four distinct blade configuration, five distinct blade configuration, six distinct blade configuration, seven distinct blade configuration, eight distinct blade configuration, or any range of the foregoing values. In some embodiments, the kit comprises at least two pairs of nested blade assemblies. In some embodiments, the kit comprises at least four pairs of nested blade assemblies.

In some embodiments, the retractor 100 may be provided to a surgeon or surgical personnel in the form of a kit comprising additional surgical articles and optionally instructions for the use and handling of the retractor. Such additional surgical articles may include one or more of: scalpels, suture needles, suture material, spinal implants, spinal fusion rods, graft material, biocompatible adhesive and closure staples.

In some embodiments, the blades 122, 142 may take on a variety of shapes and sizes. In some embodiments, a kit is provided comprising a plurality of retractors having blades 122, 142 of various sizes or shapes. In some embodiments, a kit is provided comprising a retractor, optionally more than two blades assemblies, at least two of which differ from one another in size or shape, and one or more implants for performing spinal surgery. Thus, a variety of surgical kits for performing surgery, especially spinal surgery, are contemplated and methods of using the retractor to perform surgery, especially spinal surgery, are contemplated.

The movement of the blades 122, 142 can cause less trauma to the tissue by gently pushing the tissue apart. The blades 122, 142 can have a low-profile configuration that can cause less trauma upon insertion. The blades 122, 142 can be moved about linear axes to reduce trauma. The blades 122, 142 can be independently actuated to reduce trauma.

Figure 15:
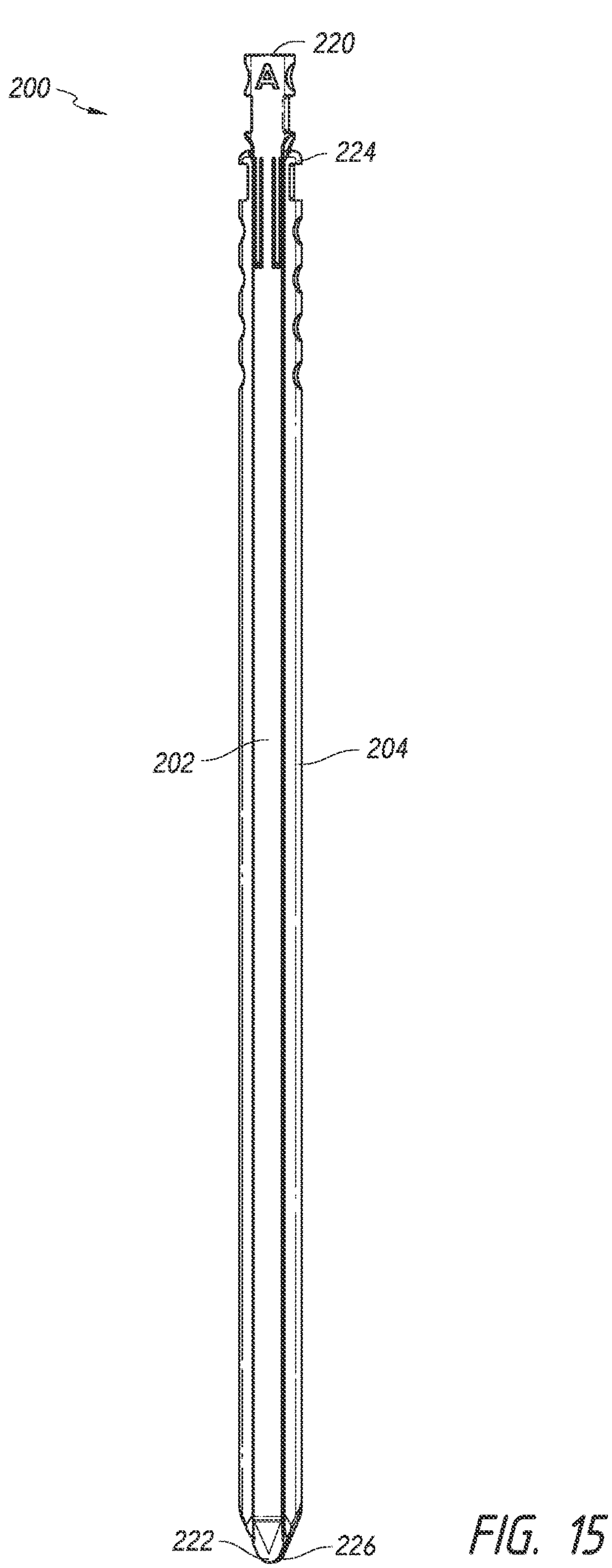
FIG. 15 provides a perspective view of a probe assembly.
Figures 16A, 16B:
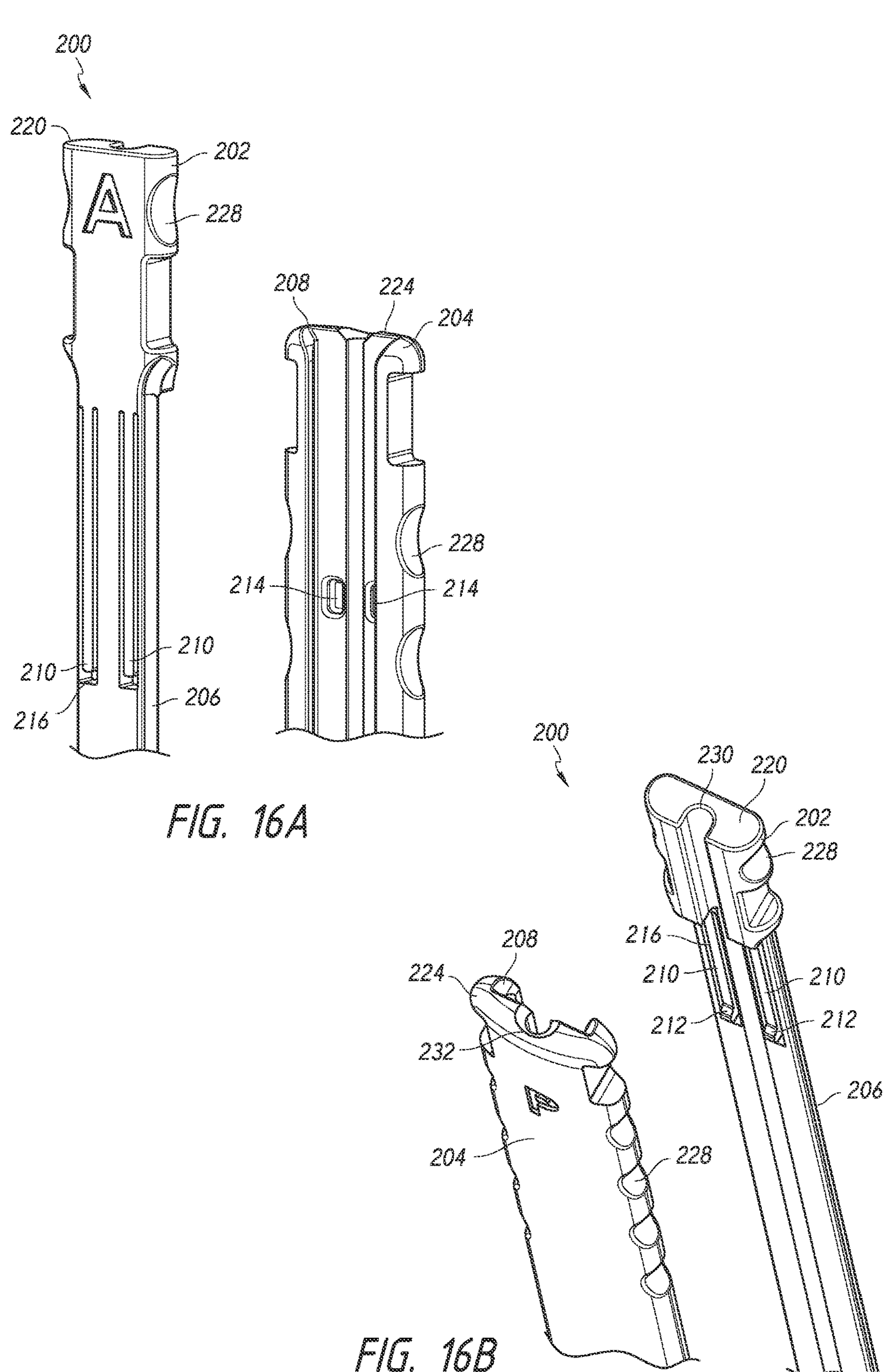
FIGS. 16A-16B provide proximal views of the probe assembly of FIG. 15.
Figure 17:
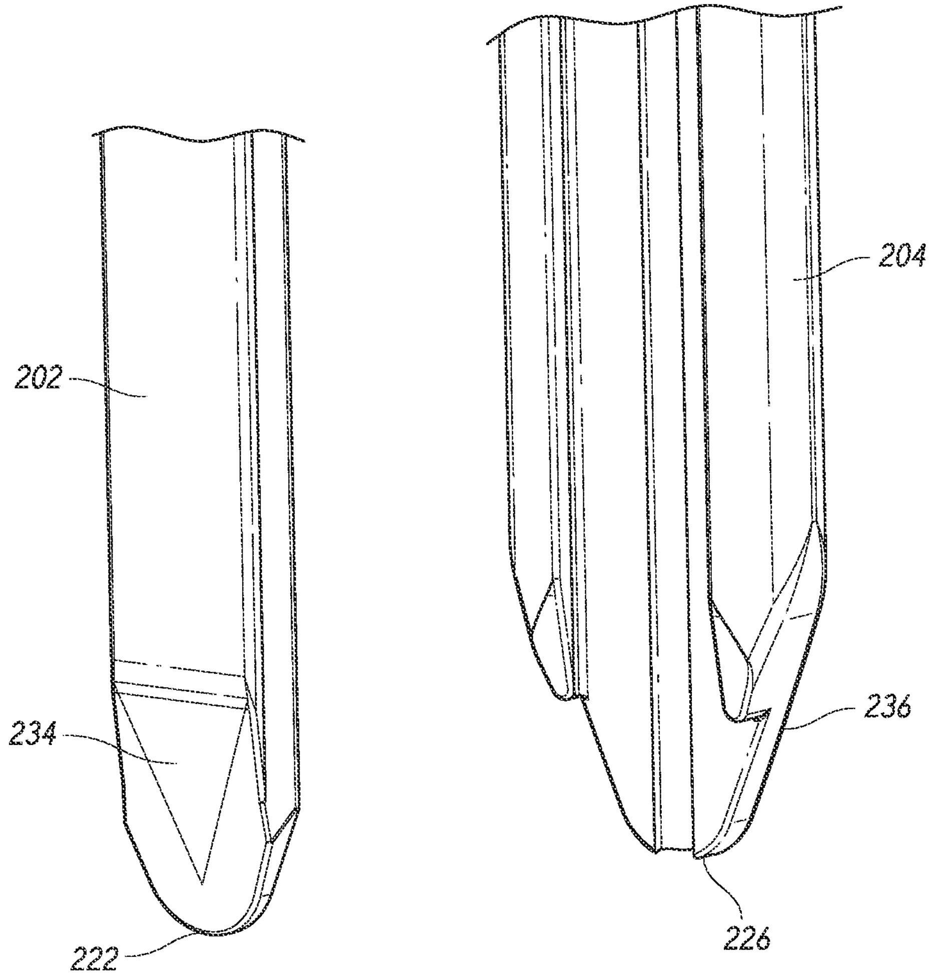
FIG. 17 provides a distal view of the probe assembly of FIG. 15.

FIGS. 15-17 illustrate a probe assembly 200. The probe assembly 200 can include an anterior probe 202. The probe assembly 200 can include a posterior probe 204.

The second blade 142 can be configured to receive the probe assembly 200. In some embodiments, the probe assembly 200 can be configured to be inserted from the second blade distal end 146. The probe assembly 200 can be configured to be inserted in a direction extending toward the body 102. In some embodiments, the probe assembly 200 can be configured to be inserted from the second blade proximal end 144. The probe assembly 200 can be configured to be inserted in a direction extending away from the body 102.

The probe assembly 200 is configured for use in conjunction with the retractor 100. The probe assembly 200 can be utilized independently in other methods of use. The probe assembly 200 can include one or more probes. The probe assembly 200 can include one probe, two probes, three probes, four probes, or any range of two of the foregoing values. The probe assembly 200 can include the anterior probe 202 and the posterior probe 204.

The anterior probe 202 can include a sliding feature 206. The anterior probe 202 can include one sliding feature, two sliding features, three sliding features, four sliding features, or any range of two of the foregoing values. The sliding feature 206 can be a dovetail projection. The sliding feature 206 can be a tapered projection. The sliding feature 206 can be a keyed projection. The sliding feature 206 can be a locating key shape. The sliding feature 206 can be a shaped projection. The sliding feature 206 can be generally rectangular. The sliding feature 206 can have flared sides.

The posterior probe 204 can include a corresponding sliding feature 208. The posterior probe 204 can include one corresponding sliding feature, two corresponding sliding features, three corresponding sliding features, four corresponding sliding features, or any range of two of the foregoing values. The corresponding sliding feature 208 can be a dovetail groove. The corresponding sliding feature 208 can include an undercut. The corresponding sliding feature 208 can be a shaped recess. The corresponding sliding feature 208 can be a locating key groove. The corresponding sliding feature 208 can be a shaped groove. The corresponding sliding feature 208 can be generally rectangular. The corresponding sliding feature 208 can have flared sides.

The corresponding sliding feature 208 can be configured to interlock with the sliding feature 206 of the anterior probe 202. The sliding feature 206 of the anterior probe 202 can be engaged by the corresponding sliding feature 208 of the posterior probe. The sliding feature 206 and the corresponding sliding feature 208 can have a corresponding shape to allow sliding. The sliding feature 206 and the corresponding sliding feature 208 can have a corresponding shape to prevent or limit rotation. The posterior probe 204 can include a mating configuration with the anterior probe 202. The mating configuration can be a tongue and groove configuration. In some embodiments, the posterior probe 204 can include a groove and the anterior probe 202 can include a tongue.

The anterior probe 202 can include one or more latch arms 210. The anterior probe 202 can include two latch arms 210. The latch arms 210 can be adjacent to each other. The latch arms 210 can be spaced apart. The latch arms 210 can be generally parallel. Each latch arm 210 can include an alignment feature 212. The alignment feature 212 can be a projection. The alignment feature 212 can be a wedge. The alignment feature 212 can be a stop. The alignment feature 212 can be a tab.

The posterior probe 204 can include one or more corresponding alignment features 214. The corresponding alignment features 214 can be adjacent to each other. The corresponding alignment features 214 can be spaced apart. The corresponding alignment feature 214 can be generally parallel. The corresponding alignment features 214 can be a groove. The corresponding alignment features 214 can be a passageway. The corresponding alignment features 214 can extend through the posterior probe 204. The corresponding alignment features 214 can extend partially through the posterior probe 204.

The one or more latch arms 210 can be configured to flex. The one or more latch arms 210 can be configured to pivot. Each latch arm 210 can be defined by a slot 216. The slot 216 can extend around a portion of the latch arm 210. The slot 216 can extend around three sides of the latch arm 210. The slot 216 can allow the latch arm 210 to flex. The latch arm 210 can flex to engage or disengage the alignment feature 212 of the latch arm 210 with the corresponding alignment features 214 of the posterior probe 204. The corresponding alignment features 214 of the posterior probe 204 can be engaged by the alignment features 212 of the latch arms 210.

The anterior probe 202 can include a proximal end 220 and a distal end 222. The latch arm 210 can be positioned closer to the proximal end 220 than the distal end 222. The posterior probe 204 can include a proximal end 224 and a distal end 226. The corresponding alignment features 214 can be positioned closer to the proximal end 224 than the distal end 226.

In some methods, the distal end 222 of the anterior probe 202 is inserted into the proximal end 224 of the posterior probe 204. The sliding feature 206 of the anterior probe 202 can be aligned with the corresponding sliding feature 208 of posterior probe 204. The proximal end 224 of the posterior probe 204 can accept the anterior probe 202. In some methods of use, the anterior probe 202 is aligned with the posterior probe 204. In some methods of use, the anterior probe 202 is slid down the length of the posterior probe 204 from the proximal end 224 of the posterior probe 204 toward the distal end 226 of the posterior probe 204.

The anterior probe 202 can slide distally relative to the posterior probe 204. The anterior probe 202 can be limited to sliding proximally and distally when the sliding feature 206 of the anterior probe 202 engages with the corresponding sliding feature 208. The latch arms 210 slide along the interior surface of the posterior probe 204. The latch arms 210 of the anterior probe 202 flex outward as the anterior probe 202 slides. The anterior probe 202 can slide distally relative to the posterior probe 204 until the alignment feature 212 of the latch arms 210 reaches the corresponding alignment feature 214 of the posterior probe 204. The alignment feature 212 engages the corresponding alignment feature 214 thereby preventing or limiting further distal movement. The alignment feature 212 engages the corresponding alignment feature 214 thereby preventing or limiting proximal movement.

The anterior probe 202 and the posterior probe 204 can be coupled. The anterior probe 202 and the posterior probe 204 can be translationally fixed relative to each other. The anterior probe 202 and the posterior probe 204 can be rotationally fixed relative to each other. The anterior probe 202 and the posterior probe 204 can be in a fixed spatial relationship to each other when the alignment feature 212 engages the corresponding alignment feature 214. The alignment feature 212 and corresponding alignment feature 214 can function as a stop. The stop can be positioned near the proximal ends 220, 224.

The anterior probe 202 and the posterior probe 204 can include finger grips 228. The finger grips 228 can allow the user to manipulate the anterior probe 202 and the posterior probe 204. The finger grips 228 can be positioned near the proximal ends 220, 224. The finger grips 228 can facilitate the application of force to decouple the anterior probe 202 and the posterior probe 204. The user can pull the anterior probe 202 proximally relative to the posterior probe 204. The force from the user can overcome the connection between the alignment feature 212 and the corresponding alignment feature 214. The alignment feature 212 can disengage the corresponding alignment feature 214 due to the proximal movement of the anterior probe 202.

The probe assembly 200 can be configured for use in conjunction with a k-wire. The k-wire can be a thin metallic wire or pin. The k-wire can include a tip. The tip can be pointed or sharpened. The k-wire can be anchored at a surgical site. The k-wire can be impacted into bone. The k-wire can have a diameter of 0.9 mm, 1.0 mm, 1.1 mm, 1.2 mm, 1.3 mm, 1.4 mm, 1.5 mm, or any range of the foregoing values. The anterior probe 202 and the posterior probe 204 can be sized to receive the k-wire. The anterior probe 202 and the posterior probe 204 can be inserted over the k-wire when the k-wire is positioned. The anterior probe 202 can include a first passageway 230. The first passageway 230 forms a portion of a circle. The first passageway 230 forms a minority portion of a circle. The first passageway 230 forms an arc. The first passageway 230 can extend the length of the anterior probe 202 from the proximal end 220 to the distal end 222. The posterior probe 204 can include a second passageway 232. The second passageway 232 forms a portion of a circle. The second passageway 232 forms a majority portion of a circle. The second passageway 232 forms an arc. The second passageway 232 can extend the length of the posterior probe 204 from the proximal end 224 to the distal end 226. The first passageway 230 and the second passageway 232 can form a lumen configured to receive the k-wire. The first passageway 230 and the second passageway 232 can form a circular lumen when the anterior probe 202 and the posterior probe 204 mate.

The anterior probe 202 and the posterior probe 204 can be configured to mate. The distal ends 222, 226 can form a shaped end. The probes 202, 204 can form a shape having a smooth perimeter. The smooth perimeter can form a generally flat shape such as a shape having two or more generally flat sides. In some embodiments, each probe 202, 204 forms generally half of the perimeter. In some embodiments, the posterior probe 204 forms greater than half of the perimeter. The anterior probe 202 and the posterior probe 204 can have different lengths. The anterior probe 202 can have a greater length. The anterior probe 202 and the posterior probe 204 can have different thicknesses. The posterior probe 204 can have a greater thickness. The anterior probe 202 and the posterior probe 204 can have different widths. The posterior probe 204 can have a greater width.

In some embodiments, the anterior probe 202 includes an anterior electrode 234. In some embodiments, the posterior probe 204 includes a posterior electrode 236. The electrodes 234, 236 can be on an exterior surface of the probes 202, 204. The electrodes 234, 236 can be on a distal surface of the probes 202, 204. The electrodes 234, 236 can face outward from the probes 202, 204. The electrodes 234, 236 can be positioned at any radial distance relative to each other including 90 degrees apart, 100 degrees apart, 110 degrees apart, 120 degrees apart, 130 degrees apart, 140 degrees apart, 150 degrees apart, 160 degrees apart, 170 degrees apart, 180 degrees apart, or any range of two of the foregoing values. In some embodiments, the electrodes 234, 236 are on opposed surfaces. The anterior electrode 234 can monitor the anterior side of the probes 202, 204 and the posterior electrode 236 can monitor the posterior side of the probes 202, 204.

In some methods of use, the anterior probe 202 is slid until the anterior electrode 234 aligns with the posterior electrode 236. The anterior electrode 234 aligns with the posterior electrode 236 when the alignment feature 212 and the corresponding alignment feature 214 engage. The anterior electrode 234 and the posterior electrode 236 can be diametrically opposed when the anterior probe 202 and the posterior probe 204 are mated.

The structure of the probes 202, 204 when coupled together can facilitate its passage through tissues of a patient. The patient can be positioned for any approach to the spine. The structure of the probes 202, 204 can pass through and separate the psoas muscles. The psoas muscles can run parallel to the flat surfaces of the probes 202, 204. The generally flat shape of the probes 202, 204 can dissect and/or dilate the tissues of a patient by separating the psoas muscle along the muscle fibers in a lateral approach to the spine. The flat surfaces of the probes 202, 204 can be oriented parallel to the lengths of the muscle fibers. The probes 202, 204 can be generally aligned with the muscle fibers. This orientation can help to minimize trauma to the muscle tissue as the probes 202, 204 are inserted through the psoas muscle.

The alignment feature 212 and the corresponding alignment feature 214 can function as a retention configuration. The retention configuration can maintain the position of the anterior probe 202 relative to the posterior probe 204. In some embodiments, the latch arm 210 can be formed within the anterior probe 202. The latch arm 210 can be integrally or monolithically formed with the anterior probe 202. The corresponding alignment features 214 can be formed within the posterior probe 204. The corresponding alignment features 214 can be integrally or monolithically formed with the posterior probe 204. The alignment features 212 and the corresponding alignment features 214 engage, thereby limiting further distal movement of the anterior probe 202. In some methods of use, the anterior probe 202 is slid down the length of the posterior probe 204 until the anterior probe 202 abuts a stop. The mating configuration can couple other components of the probe assembly 200 with the one or more of the probes 202, 204

Figure 18:
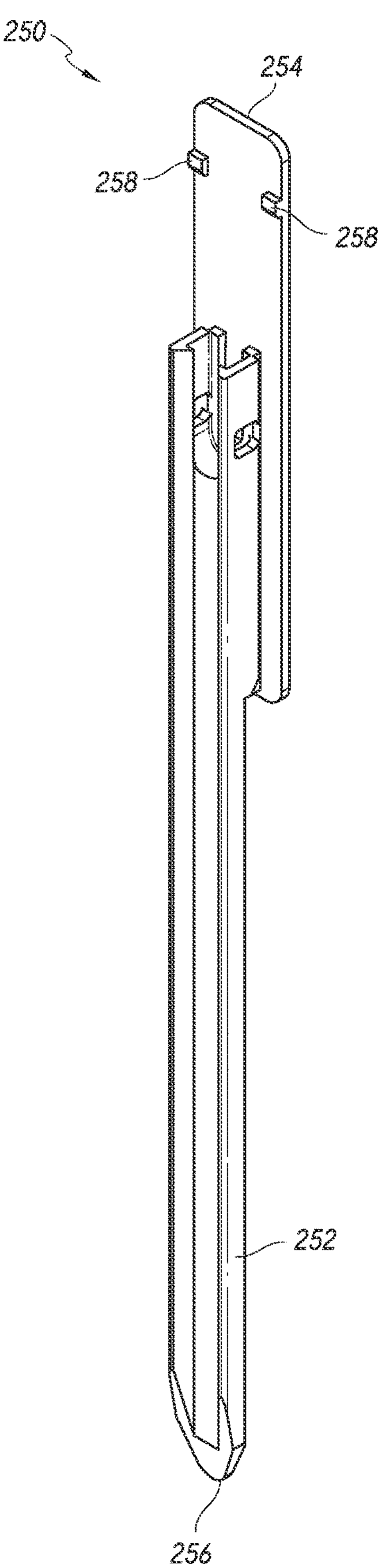
FIG. 18 provides a perspective view of a shim.

FIG. 18 illustrates a shim 250. The shim 250 can include a sliding feature 252. The shim 250 can include one sliding feature, two sliding features, three sliding features, four sliding features, or any range of two of the foregoing values. The sliding feature 252 can be a dovetail projection. The sliding feature 252 can be a tapered projection. The sliding feature 252 can be a keyed projection. The sliding feature 252 can be a locating key shape. The sliding feature 252 can be a shaped projection. The sliding feature 252 can be generally rectangular. The sliding feature 252 can have flared sides. The sliding feature 252 can be a tongue for a tongue and groove arrangement. The sliding feature 252 of the shim 250 and the sliding feature 206 of the anterior probe 202 can be the same or similar. In some embodiments, the posterior probe 204 can include the corresponding sliding feature 208. The sliding feature 252 of the shim 250 and the corresponding sliding feature 208 of the posterior probe can be configured to engage. The shim 250 can include a proximal end 254 and a distal end 256.

In some methods, the distal end 256 of the shim 250 is inserted into the proximal end 224 of the posterior probe 204. The sliding feature 252 of the shim 250 can be aligned with the corresponding sliding feature 208 of posterior probe 204. The proximal end 224 of the posterior probe 204 can accept the shim 250. In some methods of use, the shim 250 is aligned with the posterior probe 204. In some methods of use, the shim 250 is slid down the length of the posterior probe 204 from the proximal end 224 of the posterior probe 204 toward the distal end 226 of the posterior probe 204. The shim 250 can slide distally relative to the posterior probe 204.

In some embodiments, the shim 250 is configured to couple with the second blade 142 instead of, or in addition to the posterior probe 204. The shim 250 can include an alignment feature 258. The alignment feature 258 can include protrusions. The second blade 142 can include a corresponding alignment feature 260 as shown in FIG. 6. The corresponding alignment feature 260 can include grooves. The alignment feature 258 can engage the corresponding alignment feature 260 as the shim 250 slides relative to the second blade 142.

In some embodiments, the second blade 142 can include the longitudinally extending slot 160. The longitudinally extending slot 160 is sized to accept one or more probes 202, 204. In some embodiments, the longitudinally extending slot 160 is sized to accept the anterior probe 202 coupled to the posterior probe 204. The longitudinally extending slot 160 and the channel 162 is sized to accept the shim 250 coupled to the posterior probe 204. In some embodiments, the posterior probe 202 can form greater than half of the perimeter of the mated probes 202, 204. The longitudinally extending slot 160 can limit motion of the anterior probe 202 and the posterior probe 204 in directions other than translation. The longitudinally extending slot 160 can limit motion of the posterior probe 204 after the anterior probe 202 is removed. The longitudinally extending slot 160 can limit motion of the posterior probe 204 after the shim 250 is inserted.

Figure 19:
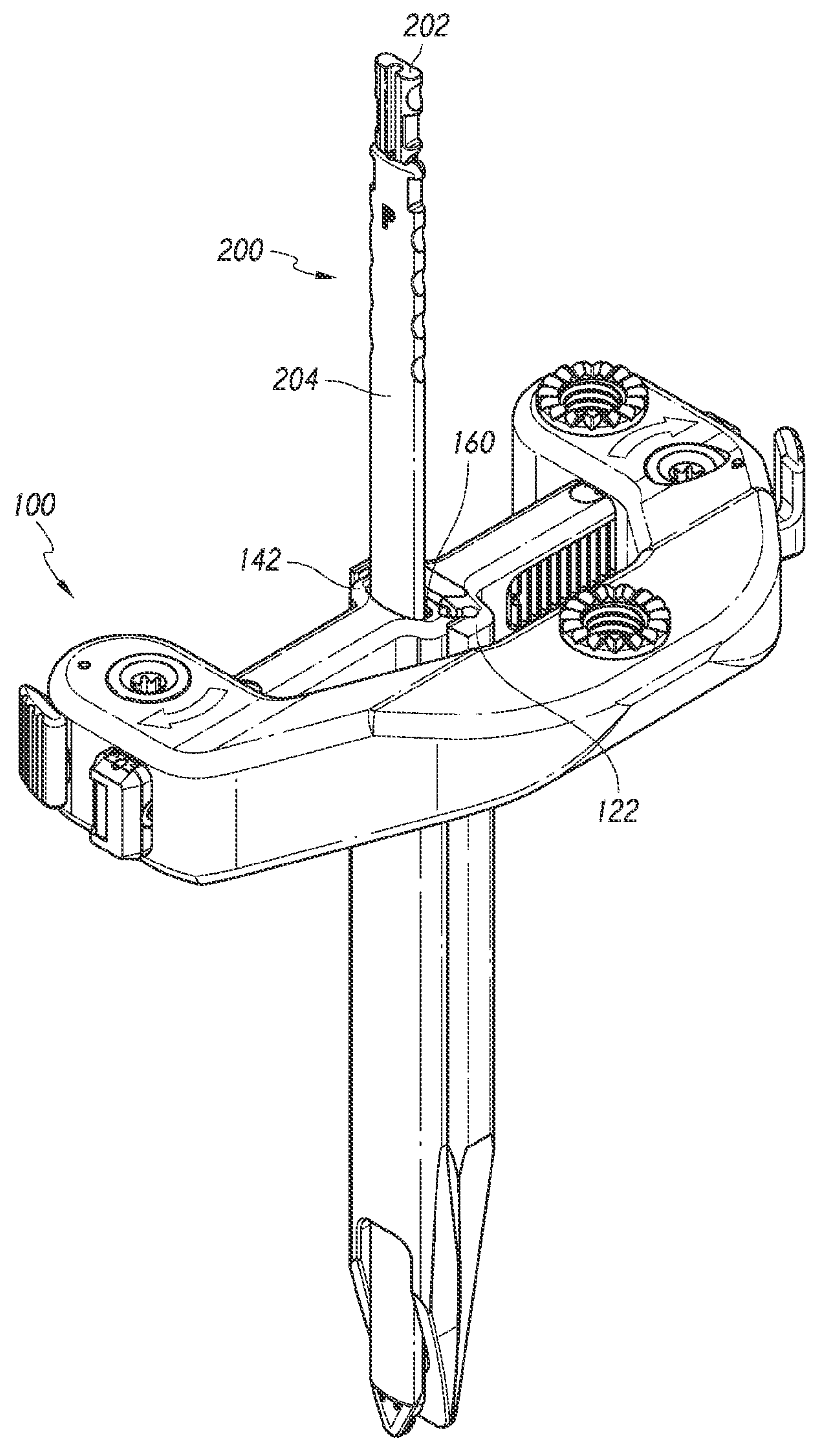
FIG. 19 provides a perspective view of the retractor of FIG. 1 and the probe assembly of FIG. 15 with the blades in a closed position.
Figure 20:
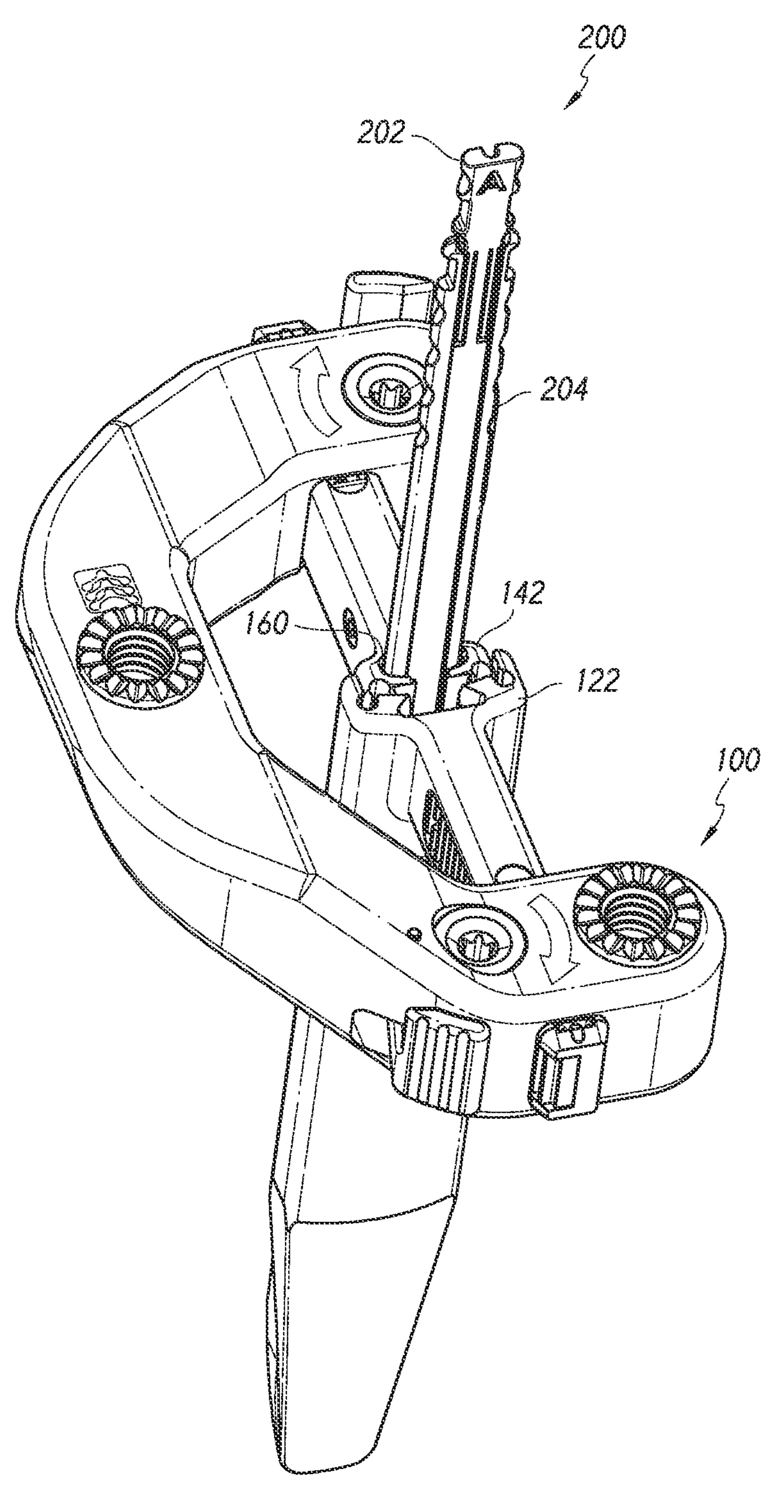
FIG. 20 provides another perspective view of the retractor of FIG. 1 and the probe assembly of FIG. 15 with the blades in a closed position.
Figure 21:
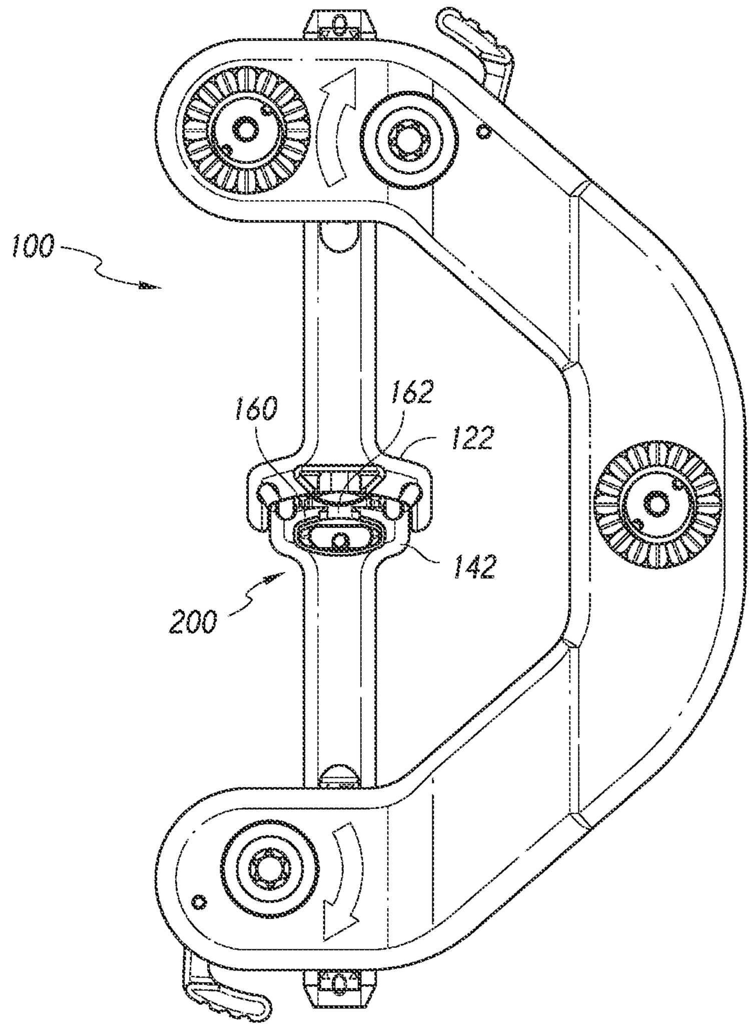
FIG. 21 provides a top view of the retractor of FIG. 1 and the probe assembly of FIG. 15 with the blades in a closed position.
Figure 22:
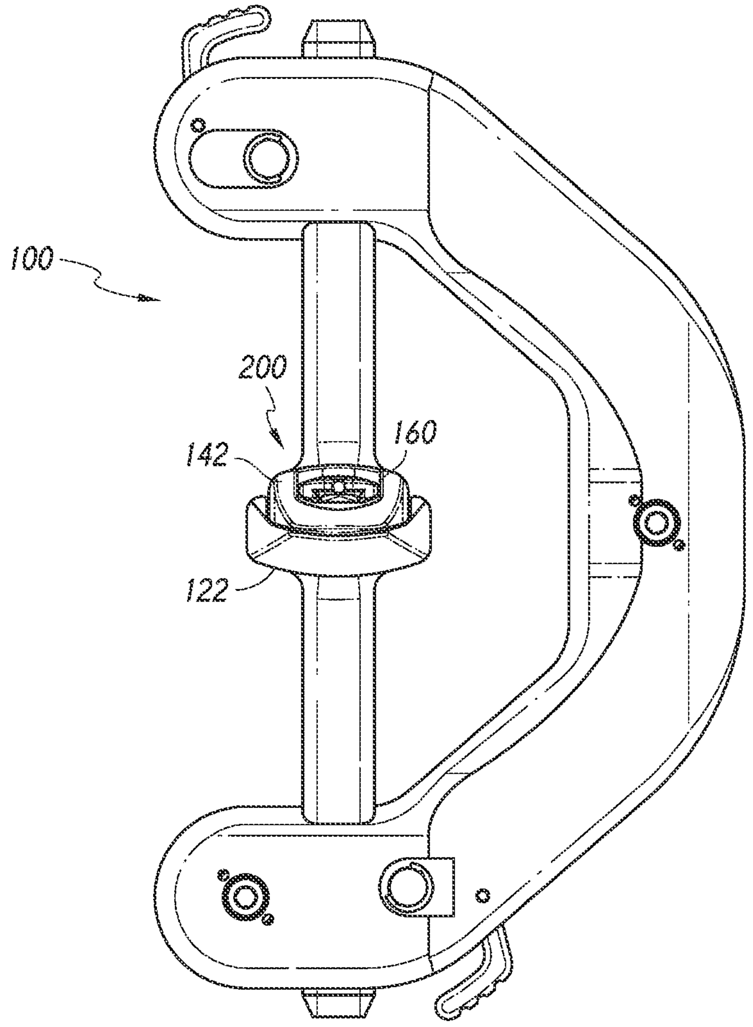
FIG. 22 provides a bottom view of the retractor of FIG. 1 and the probe assembly of FIG. 15 with the blades in a closed position.

FIGS. 19-22 illustrate a probe system 200 and a method for its use in conjunction with the retractor 100. FIG. 19 illustrates a perspective view of the retractor 100 and the probe assembly 200 with the blades 122, 142 in a closed position. FIG. 20 illustrates another perspective view of the retractor 100 and the probe assembly 200 with the blades 122, 142 in a closed position. FIG. 21 illustrates a top view of the retractor 100 and the probe assembly 200 with the blades 122, 142 in a closed position. FIG. 22 provides a bottom view of the retractor 100 and the probe assembly 200 with the blades 122, 142 in a closed position.

The probes 202, 204 can form a shape having a smooth perimeter. The smooth perimeter can form a generally flat shape such as a shape having two or more generally flat sides. In some embodiments, the anterior probe 202 includes an anterior electrode 234. In some embodiments, the posterior probe 204 includes a posterior electrode 236. The posterior probe 204 can include a mating configuration with the anterior probe 202. The structure of the probes 202, 204 when coupled together can facilitate its passage through tissues and muscles which can run parallel to the exterior surfaces of the probes 202, 204. The structure of the probes 202, 204 when coupled together can facilitate its passage through tissues and muscles which can run parallel to the generally flat sides of the probes 202, 204. The elongate shape of the probes 202, 204 can dissect and/or dilate the tissues and muscles of a patient along the muscle fibers. The exterior surfaces of the probes 202, 204 can be oriented parallel to the lengths of the muscle fibers. The generally flat sides of the probes 202, 204 can be oriented parallel to the lengths of the muscle fibers.

In some methods of use, the probes 202, 204 are coupled before insertion. The posterior probe 204 can include a retention configuration with the anterior probe 202. The retention configuration can maintain the position of the anterior probe 202 relative to the posterior probe 204 during insertion. In some methods of use, an incision is made on the patient. In some methods of use, the anterior probe 202 and the posterior probe 204 are inserted into a patient, preferably into an anchorable location, such as a collagenous tissue, bone, or vertebral disc. In some methods of use, the posterior probe 202 and the anterior probe 204 are coupled with the mating configuration prior to insertion within the patient. The probes 202, 204 can be configured to be inserted while assembled together. In some methods, the posterior probe 204 is inserted first. The anterior probe 202 is slid along the length of the posterior probe 204 toward the anchorable location.

In some methods of use, the probes 202, 204 are inserted before the retractor 100. In some embodiments, the first blade 122 can include the longitudinally extending slot 160. The longitudinally extending slot 160 can be sized to accept one or more probes 202, 204. In some embodiments, the longitudinally extending slot 160 is sized to accept the anterior probe 202 coupled to the posterior probe 204. The longitudinally extending slot 160 can limit motion of the probes 202, 204 in directions other than translation.

The retractor 100 can be lowered relative to the mated probes 202, 204. The probes 202, 204 can be inserted underneath the first blade 122. The probes 202, 204 can be inserted from the distal end 126 of the first blade 122. The probe assembly 200 can be configured to slide into the longitudinally extending slot 160 of the first blade 122. In some methods of use, the probes 202, 204 are aligned with the first blade 122. In some methods of use, the first blade 122 is slid down the length of the probes 202, 204 from the proximal end 220, 224 of the probes 202, 204 toward the surgical site. The longitudinally extending slot 160 of the first blade 122 can fit substantially closely around the probes 202, 204.

Each probe 202, 204 can have a probe body extending between the proximal end 220, 224 and the distal end 222, 226. The distal end 222, 226 can include a tip for insertion within the anchorable location. In some embodiments, the distal end 222, 226 can include a blunt end. The distal end 222, 226 can facilitate penetration of the probe 202, 204. In some embodiments, the probe 202, 204 can have a distal end of a different shape. For example, the probe 202, 204 can be formed with a different tip or the tip can be modified in shape.

In some embodiments, probe 202, 204 coupled together can be generally circular, rounded, or oval in horizontal cross section (i.e., the plane bisecting the probe 202, 204 perpendicular to the axis formed by the proximal end 220, 224 and the distal end 222, 226). In other embodiments, the probe 202, 204 coupled together can be generally rectangular in horizontal cross section or square in horizontal cross section. Some representative cross-sectional shape of the probes 202, 204 coupled together can include: a circle; an oval; a triangle; a rectangle; a square; a polygon; a flattened oval; a thin flattened oval; a rounded rectangle; a thin rounded rectangle; a thin rectangle; ellipsoid, or any combination of the foregoing shapes. Each probe 202, 204 can form a portion of the cross-section, for instance half of the cross-section. In some embodiments, the probe 202, 204 can be any other appropriate shape. The probe 202, 204 can include a cross-sectional shape in which the corners of the probe 202, 204 are rounded. The probe 202, 204 can include an arrangement in which the adjacent sides are not exactly perpendicular (e.g., plus or minus 10 degrees, 5 degrees, 1 degrees or 0.1 degrees from perpendicular) The probe 202, 204 can include an arrangement in which the sides of the probe have ridges, bends that deviate 10%, 5%, 1% or 0.1% from the width or length of a side.

In some embodiments, the probes 202, 204 can be constructed out of a biocompatible metal, such as but not limited to stainless steel, titanium, and cobalt chrome moly. In some embodiments, the probes 202, 204 can be constructed out of a polymer material, such as PEEK or polycarbonate. In some embodiments, the probes 202, 204 can be constructed out of a material that is not conductive. In some embodiments, the probes 202, 204 can be constructed out of a biocompatible ceramic. In some embodiments, the probes 202, 204 can be constructed out of any stiff, biocompatible material, including such classes of materials as metals, ceramics, and polymers, or any combinations thereof. In some embodiments, the probes 202, 204 can be constructed out of non-biocompatible material and coated with a biocompatible material.

In some embodiments, the probes 202, 204 can have a vertical dimension (i.e., between the proximal end 220, 224 and the distal end 222, 226) about 5 cm, 10 cm, 20 cm, 30 cm, 40 cm, 50 cm, between 5 cm and 50 cm, between 10 cm and 40 cm, between 20 cm and 30 cm, or any range between two of the foregoing values. In some embodiments, the probes 202, 204 can have a vertical dimension which is appropriate to allow the probes 202, 204 to function as described herein. In some embodiments, the probes 202, 204 can have a width in its largest, non-vertical dimension, in the range of about 5 mm, 10 mm, 20 mm, 30 mm, 40 mm, 50 mm, 60 mm, 70 mm, 80 mm, 90 mm, 1 cm, 1.5 cm, 2 cm, 2.5 cm, 3 cm, 3.5 cm, 4 cm, 4.5 cm, 5 cm, between 5 mm and 1 cm, between 1 cm and 2 cm, between 5 mm and 50 mm, between 50 mm and 1.5 cm, or any range between two of the foregoing values.

In some embodiments, the distal end 222, 226 can extend horizontally in from the edges of the probes 202, 204. In some embodiments, the distal end 222, 226 can be rounded or smoothed. In some embodiments, the distal end 222, 226 can be blunt. In some embodiments, the distal end 222, 226 can be tapered. In some embodiments, the distal end 222, 226 can be beveled. In some embodiments, the distal end 222, 226 can be sharpened. In some embodiments, the distal end 222, 226 can be sharpened across their entire length to form a blade along their entire length. In some embodiments, the distal end 222, 226 can be sharpened across only a portion of their length to form a blade along only a portion of their length. In some embodiments, the distal end 222, 226 can be machined flat on the bottom. In some embodiments, the distal end 222, 226 together can form a continuous edge. In some embodiments, each probe 202, 204 forms generally half of the tip. In some embodiments, the anterior probe 202 forms greater than half of the tip. In some embodiments, the posterior probe 204 forms greater than half of the tip.

The distal ends 222, 226 can be any shape which allows anchoring of the probes 202, 204 in tissue. In some embodiments, the edges of the distal ends 222, 226 can be machined to be substantially smooth. In other embodiments, the edges of the distal ends 222, 226 can be sharpened to form a blade. In some embodiments, the distal ends 222, 226 can be substantially triangular. In other embodiments, the distal ends 222, 226 can be substantially parabolic. In some embodiments, at least a portion of the edges of the distal ends 222, 226 can be sharpened. The distal ends 222, 226 can form a blade to facilitate insertion of the probes 505, 510 into corporeal tissue of a patient.

The probe assembly 200 can be a thin, blade like probe having a generally elongate, flat cross-section. The cross-section may limit the probes 202, 204 movement within the anchorable location to detect nerve signals. In some embodiments, each probe 202, 204 includes an electrode 234, 236 to detect nerve signals. The electrodes 234, 236 can be positioned to detect nerve activity at locations approximately 180 degrees apart. The structure of the probes 202, 204 can facilitate its passage through tissues of a patient (e.g., psoas muscles) which can run parallel to the flat surfaces of the probe assembly 200.

In some embodiments, the probes 202, 204 comprise at least one electrode 234, 236. The at least one electrode 234, 236 is capable of stimulating a nerve to provoke an electromyographic response in the nerve. The probes 202, 204 can sense nerve activity with the electrodes 234, 236. The probes 202, 204 can also anchor the retractor 100 at an anchorable location. In some embodiments, only one electrode is used. In other embodiments, a plurality of electrodes can be used. The probe assembly 200, the anterior probe 202, and the posterior probe 204 can include any number of electrodes include 1, 2, 3, 4, 5, 6, 7, 8, 9, 10, between 1 and 4 electrodes, between 2 and 10 electrodes, or any range of two of the foregoing values. In some embodiments, at least one electrode can be disposed on the anterior probe 202. In some embodiments, at least one electrode can be disposed on the posterior probe 204. The electrodes 234, 236 can be space apart. The electrodes 234, 236 can sense nerve activity around the probe assembly 200. In some methods of use, one or more probes 202, 204 includes an electrode 234, 236 to monitor the patient. In some embodiment, each probe 202, 204 includes an electrode 234, 236. In some methods of use, each electrode 234, 236 monitors nerve activity. In some methods of use, the electrodes 234, 236 monitor nerve activity in opposite directions. In some methods of use, the electrodes 234, 236 monitor nerve activity in directions separated by about 30 degrees, 60 degrees, 90 degree, 120 degrees, 150 degrees, 180 degrees, 210 degrees, 240 degrees, 270 degrees, 300 degrees, 330 degrees, or any range of two of the foregoing values.

In some methods of use, the user can select a location in which they would like to use the retractor 100 to form an operative channel in the tissues of the patient. The location is preferably selected that provides adequate access to an intervertebral disc space while minimizing the risk of injury to nerves. After the user selects the location for retractor 100 placement, the user can make an incision in the skin and insert one or more of the probes 202, 204 by placing the tip against the surface of the patient. In some methods of use, the probes 202, 204 are coupled together prior to insertion. The anterior probe 202 can slide along the posterior probe 204. The sliding feature 206 of the anterior probe 202 can engage the corresponding sliding feature 208 of the posterior probe 204. The anterior probe 202 can include the latch arm 210. The alignment feature 212 of the latch arm 210 can engage the corresponding alignment feature 214 of the posterior probe 204. In some embodiments, the probe assembly 200 is preassembled prior to use. In some embodiment, the user couples the anterior probe 202 and the posterior probe 204 prior to use. In some methods, the anterior probe 202 and the posterior probe 204 are separately inserted. In some methods, the anterior probe 202 and the posterior probe 204 are coupled after one probe is inserted into the patient.

The user can apply pressure to the proximal end 220, 224 of the probes 202, 204. The user can then continue to apply pressure, thereby pushing the probes 202, 204 through the tissue of the patient, until the probes 202, 204 are fully in place. In some embodiments, an imaging modality can be used during the insertion of the probes 202, 204. As a representative, non-limiting example, X-ray fluoroscopy can be used during insertion of the probes 202, 204 to ensure correct placement. Any appropriate imaging modality can be used to monitor the placement of the probes 202, 204. In some embodiments, the user can make an incision with another instrument, such as a scalpel, prior to the insertion of the probes 202, 204. The user can insert the probes 202, 204 into the incision. In some embodiments, a k-wire can first be anchored at a location for retractor 100 placement. The probes 202, 204 can have a passageway 230, 232 extending through its longitudinal length to receive the k-wire The anterior probe 202 can include the first passageway 230. The posterior probe 204 can include the second passageway 232. The second passageway 232 forms a majority portion of a circle. The first passageway 230 and the second passageway 232 can form a lumen configured to receive the k-wire. The probes 202, 204 can slide down the k-wire during insertion. In some methods, the k-wire can provide improved accuracy in placement of the one or more probes 202, 204. In some methods, the k-wire can stabilize the one or more probes 202, 204 during insertion through the patient tissue.

In some methods, the probes 202, 204 are fully in place in a patient. The probes 202, 204 can be inserted into the side of the spinal column. The probes 202, 204 can be inserted between a first vertebra and a second vertebra, and into the disc therebetween. In some methods, the probes 202, 204 are positioned in a location in which the tip can anchor the probes 202, 204. The probes 202, 204 can be inserted into the patient until the tip has penetrated at least some distance into the disc between the first vertebra and second vertebra.

In some methods, the retractor 100 can be lowered relative to the probes 202, 204. The probes 202, 204 can be inserted before the retractor. The first blade 122 can include the longitudinally extending slot 160. The first blade 122 is aligned with the proximal end 220, 224 of the probes 202, 204. The first blade 122 is lowered relative to the anchored probes 202, 204. The longitudinally extending slot 160 of the first blade 122 can fit substantially closely around the probes 202, 204 as the first blade 122 is lowered. In some methods, the retractor 100 is preassembled prior to used. The first blade assembly 120 can be coupled to the body 102. The second blade assembly 140 can be coupled to the body 102. In some methods, the retractor 100 can be assembled during use.

FIGS. 19-22 illustrates the second blade 142 of the retractor 100 and the probes 202, 204. The second blade 142 can include the longitudinally extending slot 160 sized to accept the probes 202, 204. The second blade 142 can fit substantially closely around the probes 202, 204. The second blade 142 can be any type of blade as described above, including but not limited to a substantially flat blade. The first blade 122 can fit substantially closely around the second blade 142. The first blade 122 and the second blade 142 can form a nested configuration. The retractor 100 can be lowered relative to the probes 202, 204 when the retractor 100 is in a closed position.

In some methods of use, one or more blades of the retractor 100 are inserted over the probes 202, 204. In some methods of use, one or more blades of the retractor 100 are inserted over the probes 202, 204 after the probes 202, 204 are secured to the anatomy. In some methods of use, the second blade 142 of the retractor 100 is slid around the probes 202, 204. The second blade 142 can be slid from the proximal end 220, 224 of the probes 202, 204 toward the distal end 222, 226 of the probes 202, 204. In some methods of use, the first blade 122 and the second blade 142 of the retractor 100 are placed in their closed configuration. The first blade 122 and the second blade 142 can be coupled to the body 102. The blades 122, 142 can be in their stacked configuration when lowered relative to the probes 202, 204.

Figure 23:
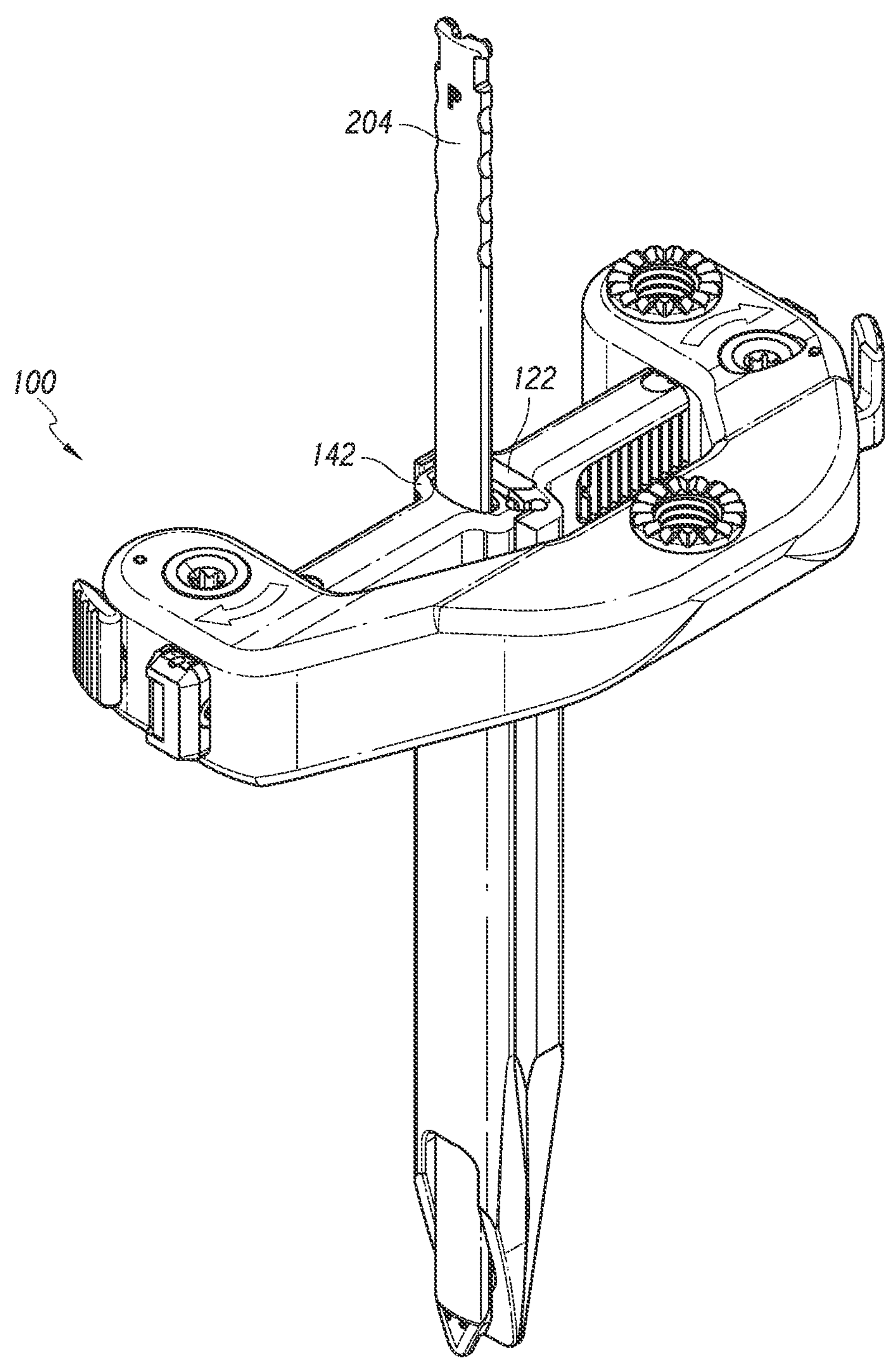
FIG. 23 provides a perspective view of the retractor of FIG. 1 and a posterior probe of the probe assembly of FIG. 15 with the blades in a closed position.
Figure 24:
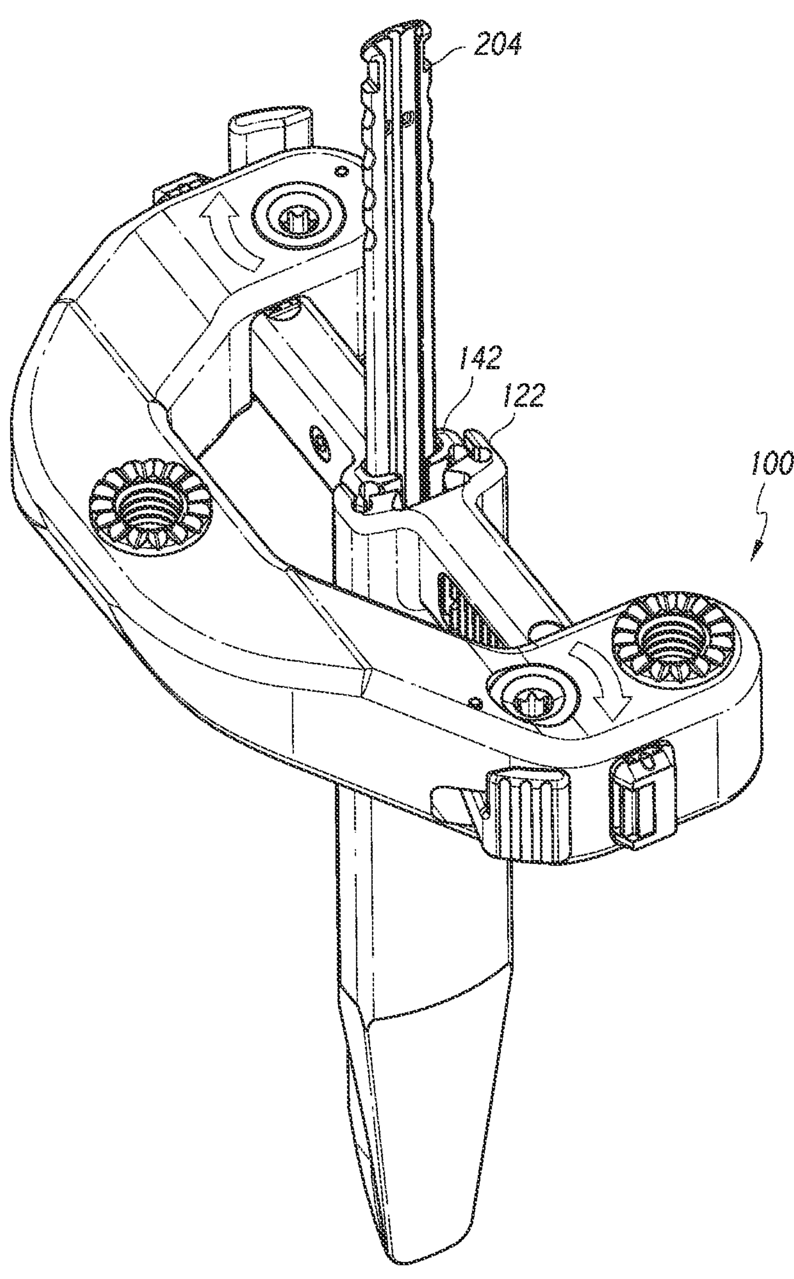
FIG. 24 provides another perspective view of the retractor of FIG. 1 and the posterior probe of the probe assembly of FIG. 15 with the blades in a closed position.
Figure 25:
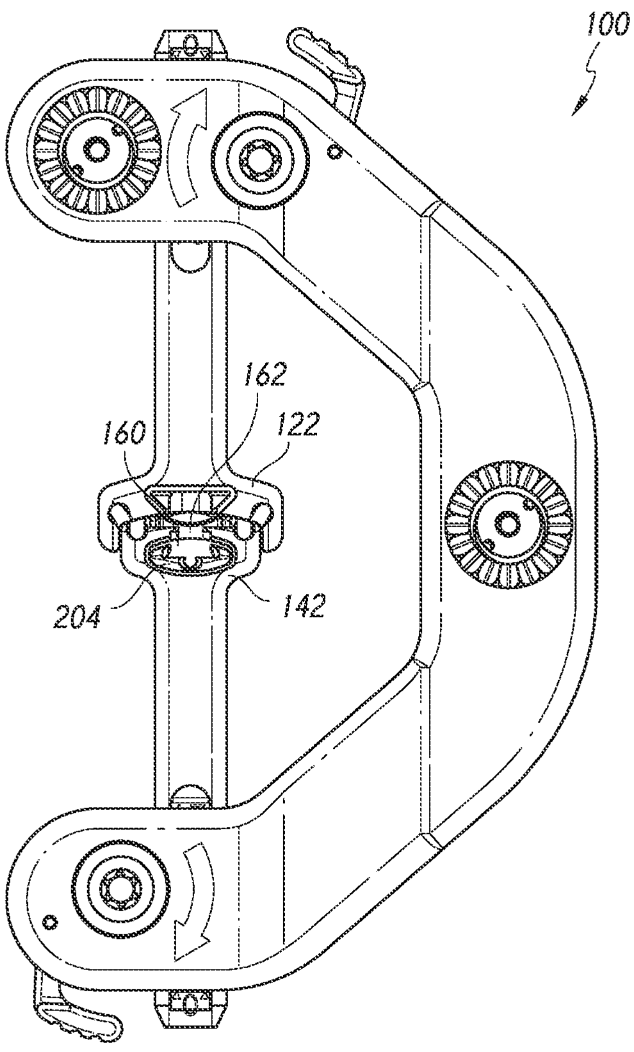
FIG. 25 provides a top view of the retractor of FIG. 1 and the posterior probe of the probe assembly of FIG. 15 with the blades in a closed position.
Figure 26:
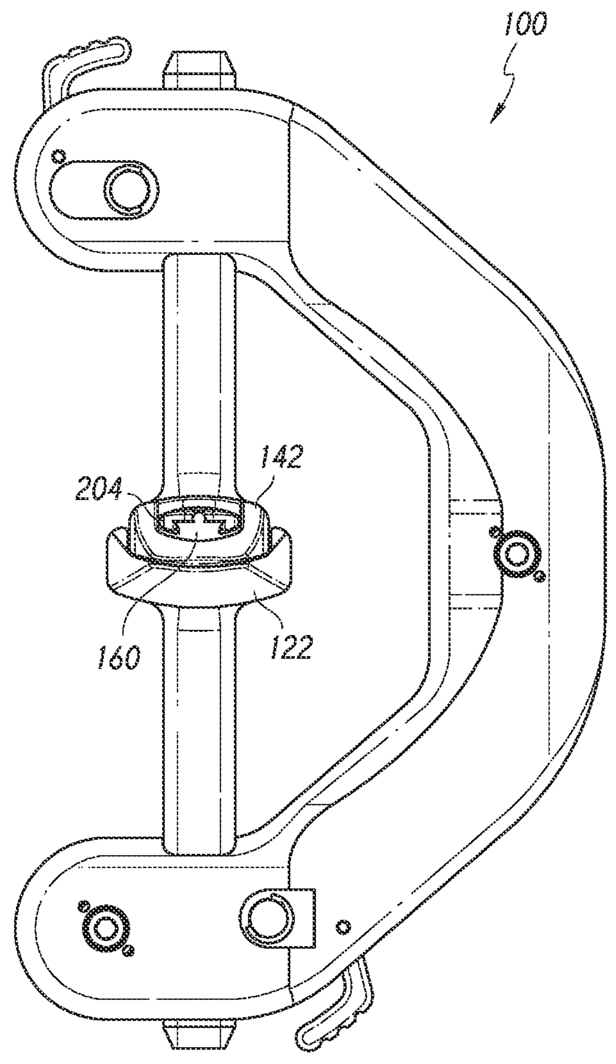
FIG. 26 provides a bottom view of the retractor of FIG. 1 and the posterior probe of the probe assembly of FIG. 15 with the blades in a closed position.

FIGS. 23-26 illustrate a method of use in conjunction with the retractor 100. FIG. 23 illustrates a perspective view of the retractor 100 and the posterior probe 204 with the blades in a closed position. FIG. 24 illustrates another perspective view of the retractor 100 and the posterior probe 204 with the blades in a closed position. FIG. 25 illustrates a top view of the retractor 100 and the posterior probe 204 with the blades in a closed position. FIG. 26 illustrates a bottom view of the retractor 100 and the posterior probe 204 with the blades in a closed position.

The anterior probe 202 can be removed after insertion of the probes 202, 204. The anterior probe 202 can slide proximally relative to the posterior probe 204. The latch arms 210 of the anterior probe 202 can disengage from the posterior probe 204. The posterior probe 204 can remain at the anchorable location. The retractor 100 can remain in place. The second blade 142 can fit substantially closely around the posterior probe 204. The first blade 122 can fit substantially closely around the second blade 142. The first blade 122 and the second blade 142 can form a nested configuration. The retractor 100 can remain in position relative to the posterior probe 204. The posterior probe 204 can form greater than half of the probe assembly 200. The posterior probe 204 can engage greater than half of the perimeter of the longitudinally extending slot 160.

Figure 27:
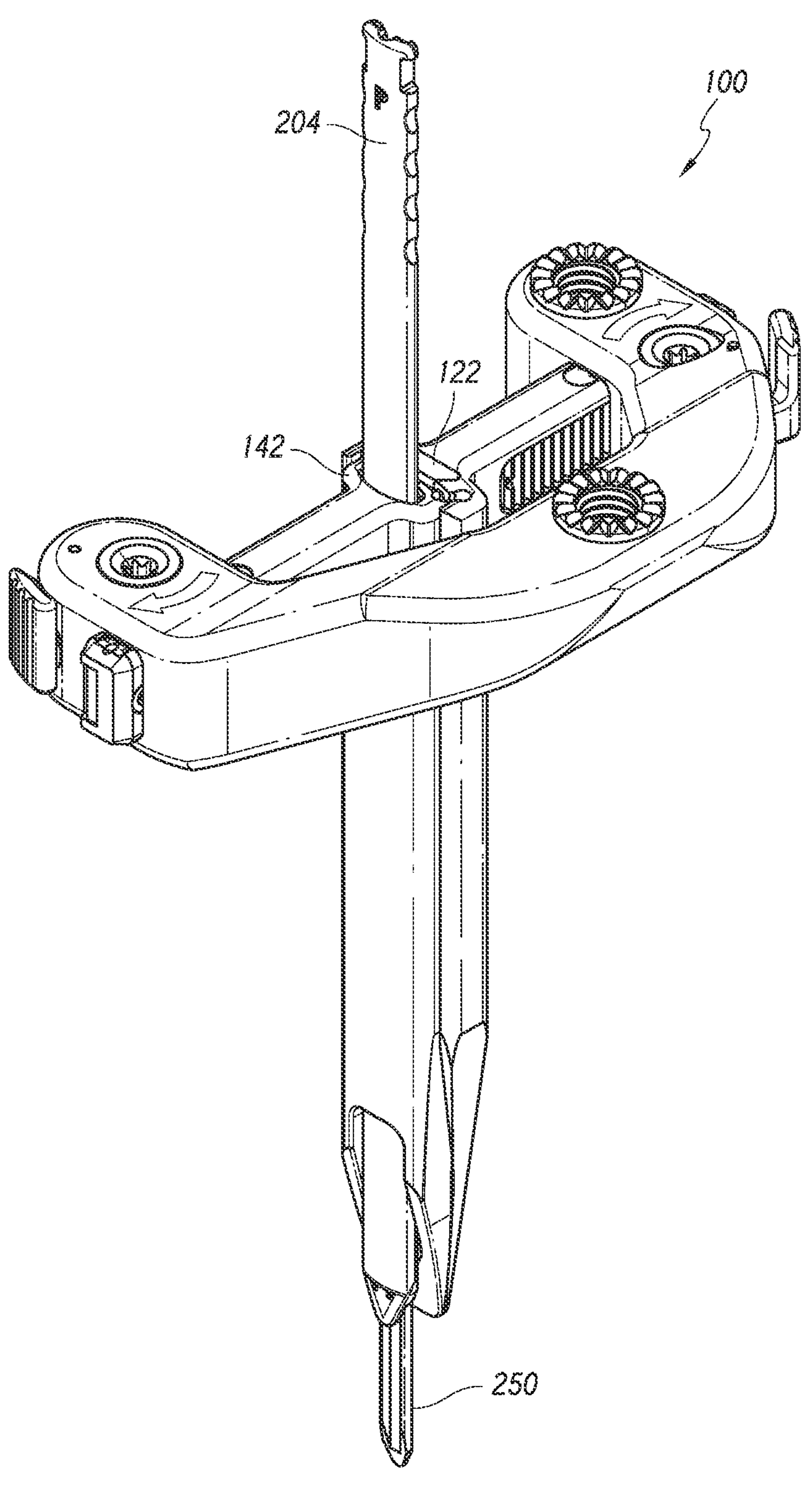
FIG. 27 provides a perspective view of the retractor of FIG. 1, a posterior probe of the probe assembly of FIG. 15, and the shim of FIG. 18 with the blades in a closed position.
Figure 28:
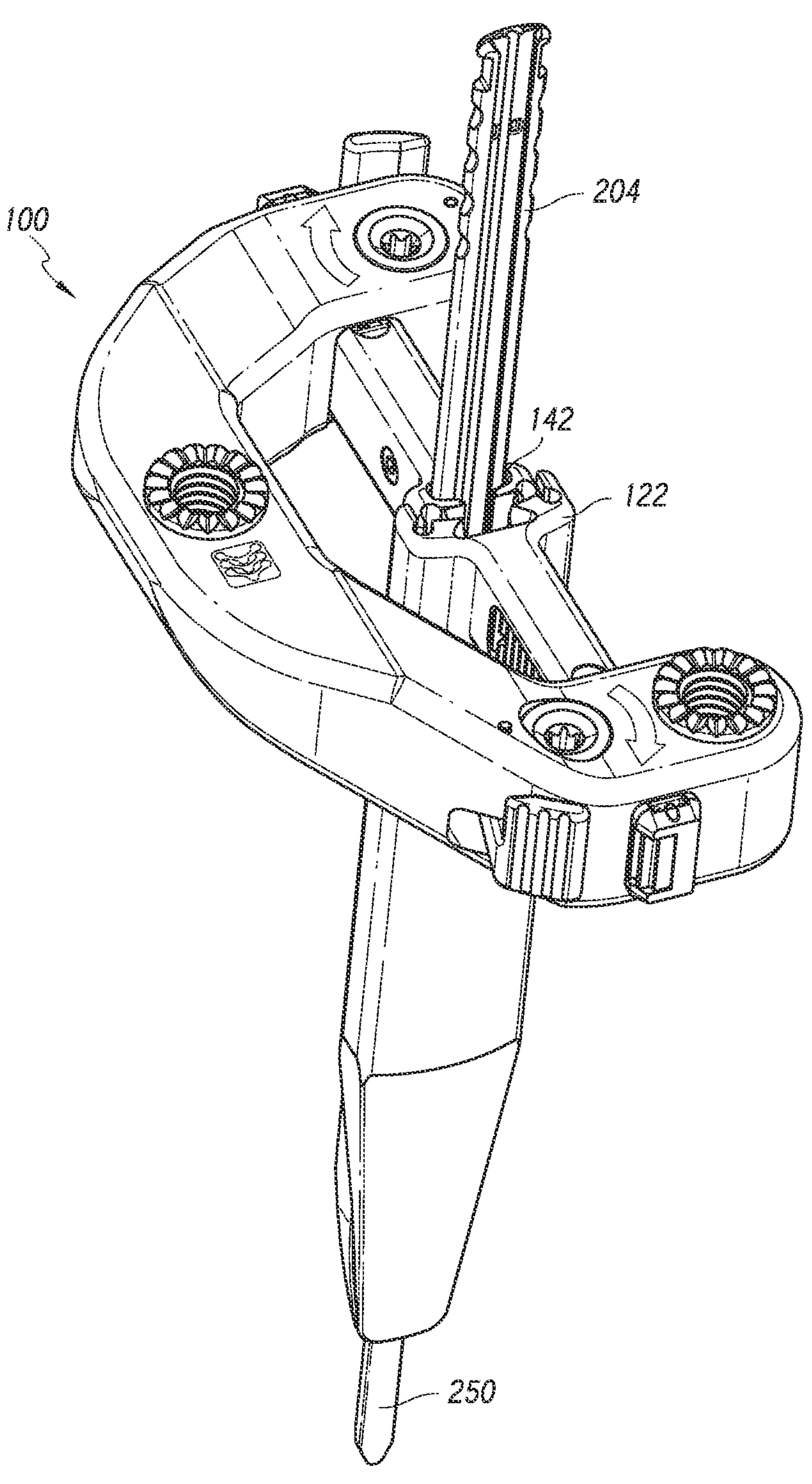
FIG. 28 provides another perspective view of the retractor of FIG. 1, the posterior probe of the probe assembly of FIG. 15, and the shim of FIG. 18 with the blades in a closed position.
Figure 29:
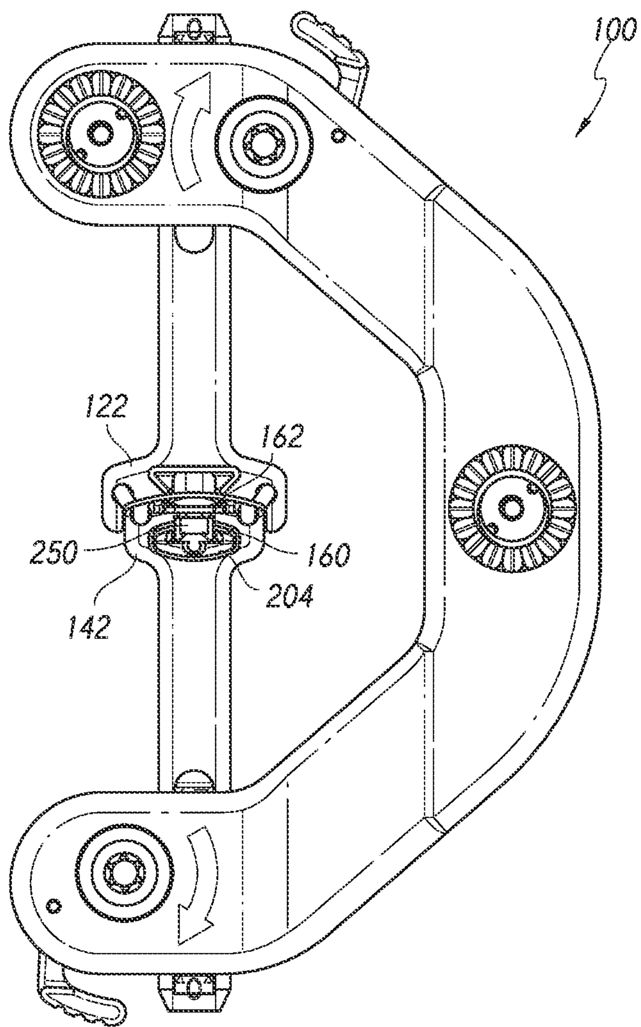
FIG. 29 provides a top view of the retractor of FIG. 1, the posterior probe of the probe assembly of FIG. 15, and the shim of FIG. 18 with the blades in a closed position.
Figure 30:
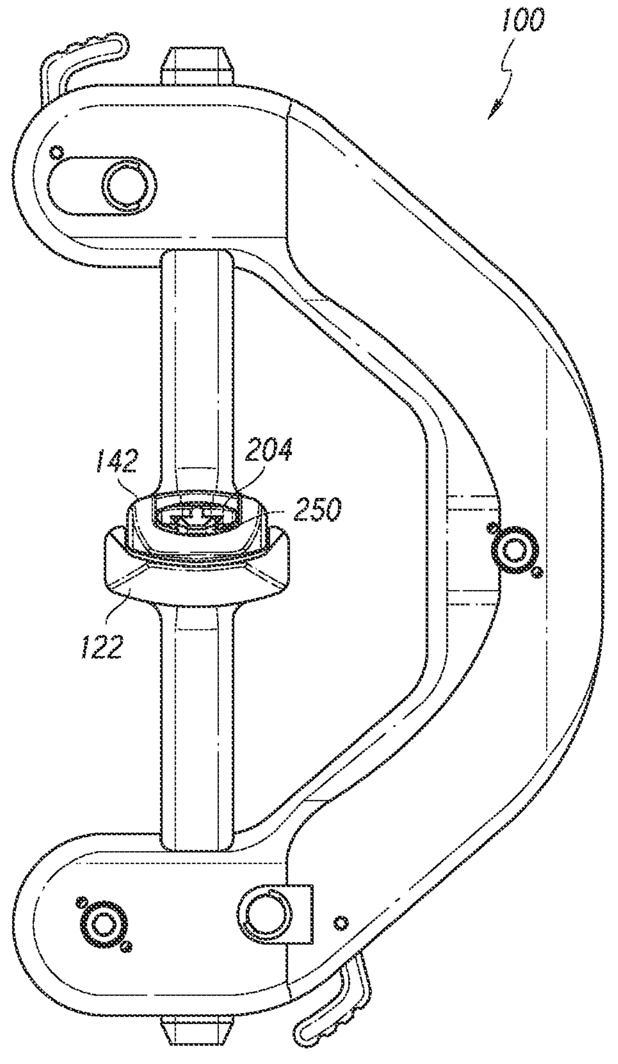
FIG. 30 provides a bottom view of the retractor of FIG. 1 and the posterior probe of the probe assembly of FIG. 15, and the shim of FIG. 18 with the blades in a closed position.

FIGS. 27-30 illustrate a method of use in conjunction with the retractor 100. FIG. 27 illustrates a perspective view of the retractor 100, the posterior probe 204, and the shim 250 with the blades in a closed position. FIG. 28 illustrates another perspective view of the retractor 100, the posterior probe 204, and the shim 250 with the blades in a closed position. FIG. 29 illustrates a top view of the retractor 100, the posterior probe 204, and the shim 250 with the blades in a closed position. FIG. 30 illustrates a bottom view of the retractor 100, the posterior probe 204, and the shim 250 with the blades in a closed position.

The shim 250 can include a sliding feature 252. In some embodiments, the posterior probe 204 can include the corresponding sliding feature 208. In some methods, the distal end 256 of the shim 250 is inserted into the proximal end 224 of the posterior probe 204. The shim 250 can slide down the length of the posterior probe 204 from the proximal end 224 of the posterior probe 204 toward the distal end 226 of the posterior probe 204. The shim 250 can extend distally relative to the posterior probe 204.

The retractor 100 can include a retention configuration with the shim 250. The shim 250 can include an alignment feature 258. The alignment feature 258 can include protrusions. The second blade 142 can include a corresponding alignment feature 260. The corresponding alignment feature 260 can include grooves. The alignment feature 258 can engage the corresponding alignment feature 260 as the shim 250 slides relative to the second blade 142. In some embodiments, the shim 250 is shorter than one or more probes 202, 204. In some embodiments, the shim 250 extends distally beyond the posterior probe 204. The shim 250 can engage the longitudinally extending slot 160. The shim 250 can engage the channel 162.

The retention configuration can maintain the position of the retractor 100 relative to the shim 250. The shim 250 can engage the second blade 142 thereby limiting further movement of the shim 250. In some methods of use, the shim 250 is slid down the length of the second blade 142 engaging and disengaging the one or more grooves of the corresponding alignment feature 260 on the second blade 142. The one or more grooves of the corresponding alignment feature 260 can be in discrete positions along the second blade 142. In some embodiments, the engagement between the alignment feature 258 and the corresponding alignment feature 260 provides feedback such as an audible click or tactile feedback for the user. Other retention configurations are also contemplated, such as detents, ratcheting hooks, and releasable clamps.

Figure 31:
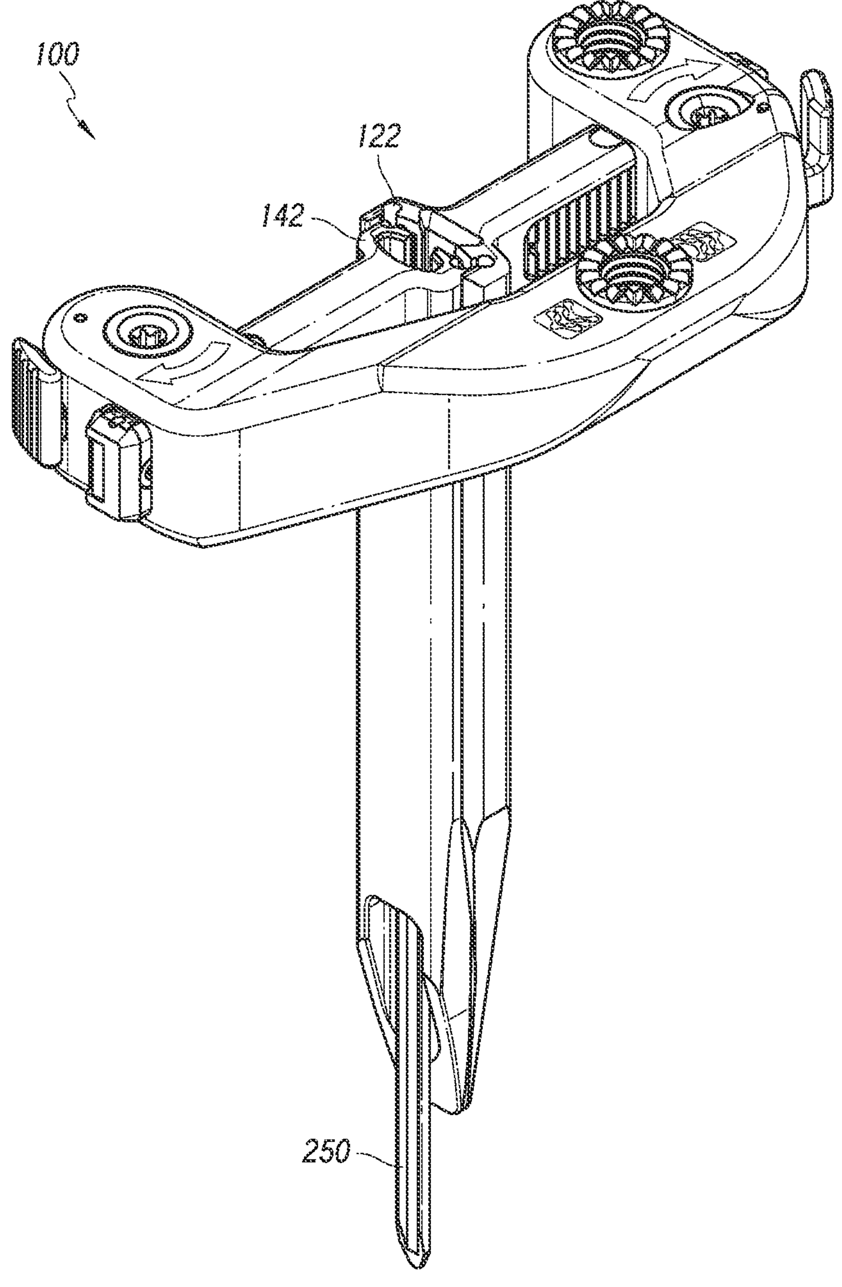
FIG. 31 provides a perspective view of the retractor of FIG. 1 and the shim of FIG. 18 with the blades in a closed position.
Figure 32:
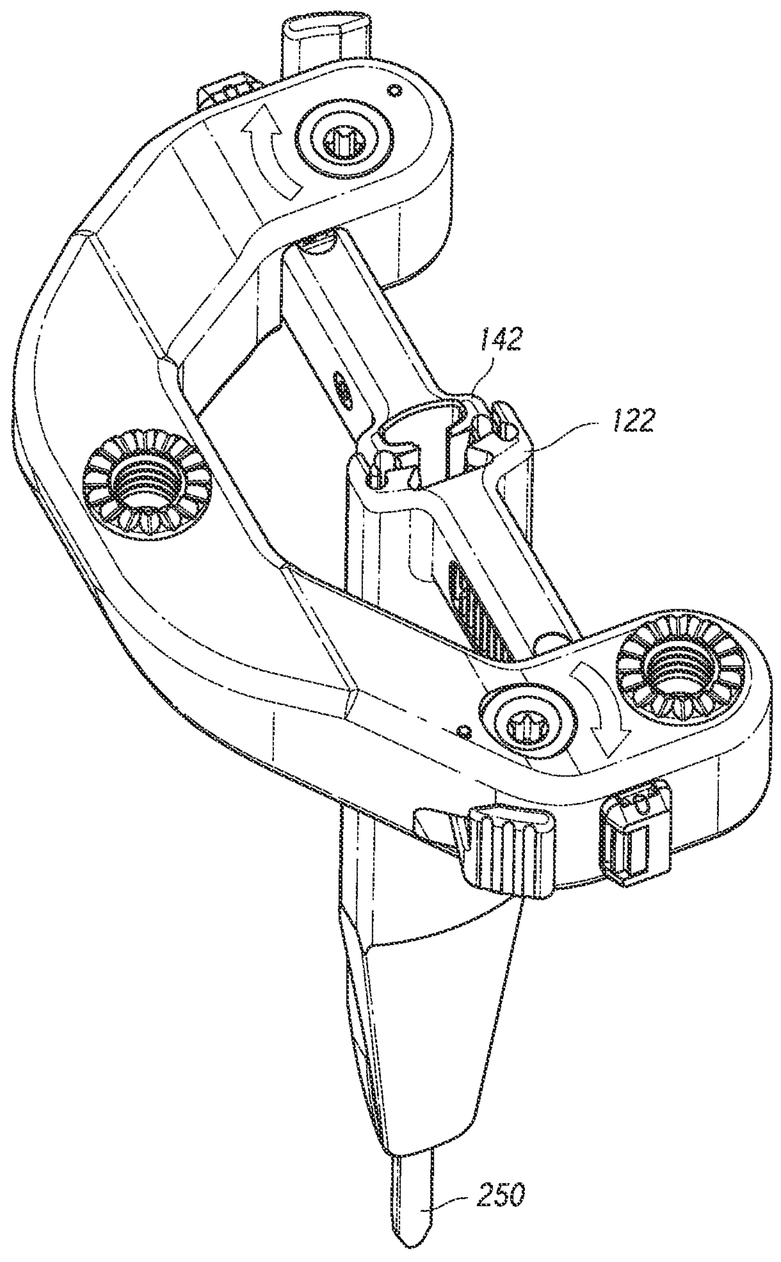
FIG. 32 provides another perspective view of the retractor of FIG. 1 and the shim of FIG. 18 with the blades in a closed position.
Figure 33:
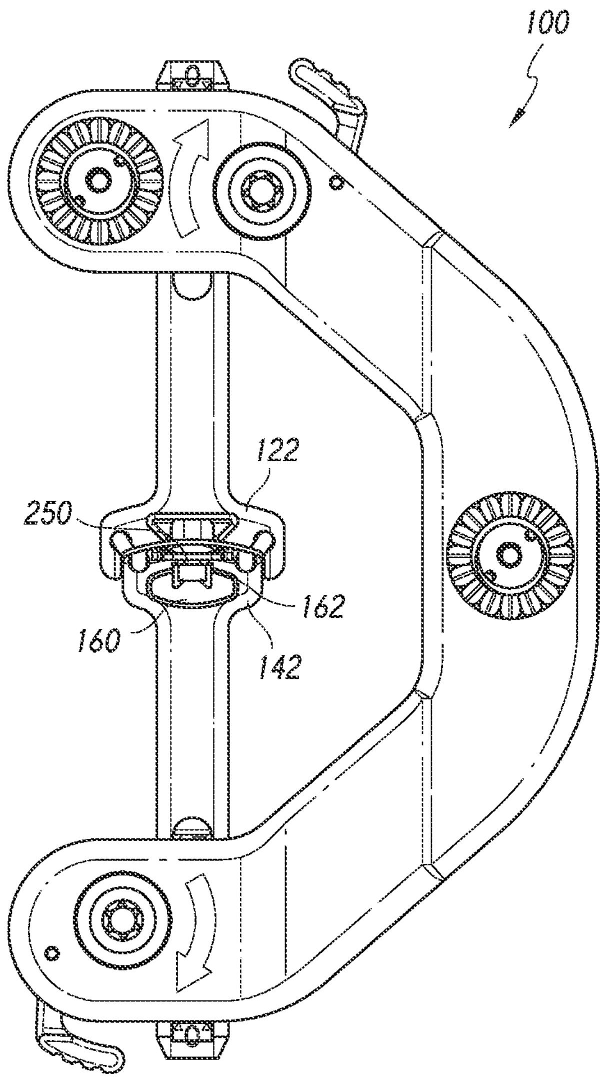
FIG. 33 provides a top view of the retractor of FIG. 1 and the shim of FIG. 18 with the blades in a closed position.
Figure 34:
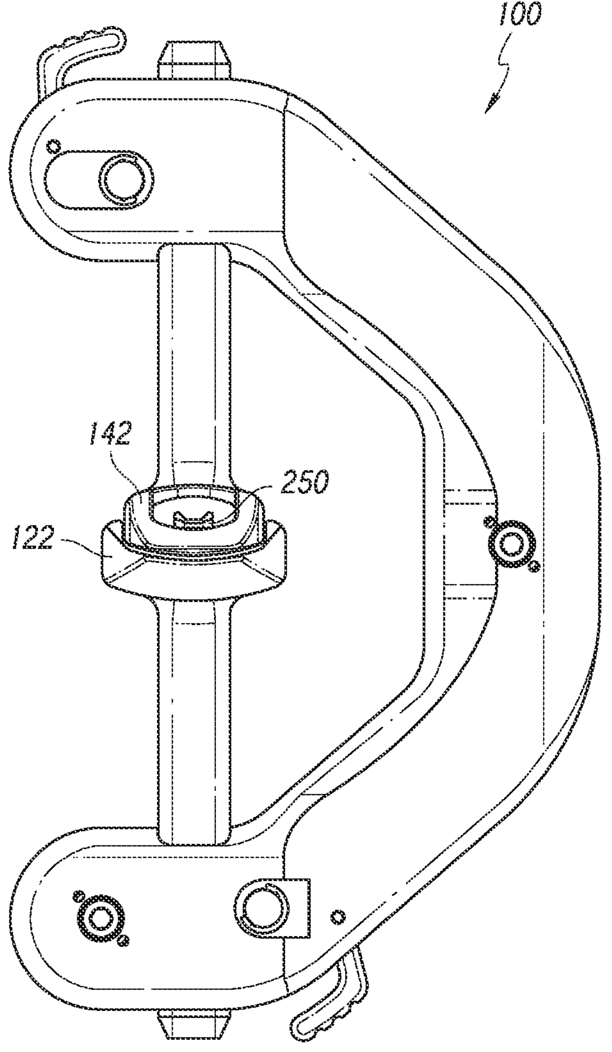
FIG. 34 provides a bottom view of the retractor of FIG. 1 and the shim of FIG. 18 with the blades in a closed position.

FIGS. 31-34 illustrate a method of use in conjunction with the retractor 100. FIG. 31 illustrates a perspective view of the retractor 100 and the shim 250 with the blades in a closed position. FIG. 32 illustrates another perspective view of the retractor 100 and the shim 250 with the blades in a closed position. FIG. 33 illustrates a top view of the retractor 100 and the shim 250 with the blades in a closed position. FIG. 34 illustrates a bottom view of the retractor 100 and the shim 250 with the blades in a closed position.

The posterior probe 204 can be removed. The posterior probe 204 can slide proximally relative to the second blade 142. The shim 250 can remain at the anchorable location. The retractor 100 can remain in place. The second blade 142 can be engaged by the shim 250. The shim 250 can extend through the longitudinally extending slot 160. The shim 250 can engage the channel 162. The shim 250 and the second blade 142 can be rigidly engaged with the alignment feature 258 and the corresponding alignment feature 260. The first blade 122 can fit substantially closely around the second blade 142. The first blade 122 and the second blade 142 can form a nested configuration. The retractor 100 can remain in position relative to the shim 250.

In some methods of use, the shim 250 can retain the retractor 100 at the anchorable location instead of the probes 202, 204. The shorter length of the shim 250 as compared to the probes 202, 204 can provide clearance around the retractor 100 for the user to work. In some methods of use, the shim 250 is held by the second blade 142 during use.

The first blade 122 and the second blade 142 of the retractor 100 can be in their closed configuration when engaged with the shim 250. The blades 122, 142 will be in their stacked configuration when coupled. The blades 122, 142 are in the closed position and aligned relatively parallel to one another.

In some methods, the retractor 100 is manipulated to achieve the opened position, as shown and described in FIGS. 7-10. In the opened position, the incision can be stretched to pull open the incision. In some methods of use, translation about the translation directions 164, 166 results in the retractor 100 opening. In some methods, the first blade 122 is moved along the translation direction 164 to open the first blade 122. In some methods, the second blade 142 is moved along the translation direction 166 to open the second blade 142. The blades 122, 142 can be opened in any order or sequence. The first blade 122 and the second blade 142 move apart from one another to open the retractor 100. The first blade 122 and the second blade 142 can be moved by rotation of the actuators 134, 154. The actuators 134, 154 rotate the gears 170, 180 which translates the corresponding racks 132, 152. The incision can be stretched open in the direction of the translation directions 164, 166.

In some methods, the retractor 100 is manipulated to achieve a closed position. The retractor can require an active close. The user can depress the first lock handle 172. The user can manually close the first blade 122. The user can push the first blade assembly 120 relative to the body 102 when the first lock handle 172 is depressed. The user can depress the second lock handle 182. The user can manually close the second blade 142. The user can push the second blade assembly 140 relative to the body 102 when the second lock handle 182 is depressed. Closing the retractor 100 can result in a final incision having substantially the same length and essentially no width, like the original incision. The retractor 100 can permit the use of a much smaller incision to create the aperture. The retractor 100 can permit less invasive surgical methods, quicker and more comfortable recovery from surgery, and potentially cost savings for the medical coverage provider.

The probes 202, 204 and the shim 250 can allow the user to easily and quickly insert a retractor 100 without cutting an incision all the way to the surgery site prior to inserting the retractor 100 into the desired location to access the surgery site. The user can quickly and easily insert the probes 202, 204 into the desired location. In some embodiments, the probes 202, 204 can sense nerve activity. In some embodiments, the probes 202, 204 can be anchored to a surgical site. In some embodiments, the probes 202, 204 are anchored using the distal ends 222, 226 in the desired location. In some embodiments, the second blade 142 of the retractor 100 is slid down one or more of the probes 202, 204. In some embodiments, the anterior probe 202 is removed and the shim 250 is inserted. In some embodiments, the shim 250 can be anchored to a surgical site. In some embodiments, the shim 250 is anchored with the distal end 256 in the desired location. In some embodiments, the posterior probe 204 is removed and the shim 250 remains during the surgical procedure. From this position, the first blade 122 can be moved in any of the ways described herein. The probes 202, 204 can be removed prior to any of these steps or left in place during the procedure.

In some embodiments, the retractor 100 and/or the probe assembly 200 comprises an endoscope, wherein the endoscope can comprise an imaging element. In some embodiments, the retractor 100 and/or the probe assembly 200 comprises a light source or is configured to receive a light source. In some embodiments, the retractor 100 and/or the probe assembly 200 can be configured to allow the user to visualize the placement of the probe assembly 200. In some embodiments, the retractor 100 and/or the probe assembly 200 can be configured to allow the user to slide a retractor 100 down over the probe assembly 200 and into place as described herein to create an operative channel.

While certain embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

What is claimed is:

1. A retractor comprising:

a first blade assembly comprising a first blade and a first rack comprising a first toothed bar;

a first actuator configured to translate the first blade along a first translation direction;

a first lock handle configured to limit translation along a direction opposite the first translation direction; and a second blade assembly comprising a second blade and a second rack comprising a second toothed bar, wherein the first rack and the second rack are aligned to translate along a common axis.

2. The retractor of claim 1, further comprising a second actuator configured to translate the second blade along a second translation direction.

3. The retractor of claim 2, wherein the first actuator and the second actuator are configured to be rotated in the same direction to open the retractor.

4. The retractor of claim 2, wherein the first actuator and the second actuator are configured to be rotated independently.

5. The retractor of claim 2, further comprising a second lock handle configured to limit translation along a direction opposite the second translation direction.

6. The retractor of claim 1, wherein the first actuator comprises a pinion.

7. The retractor of claim 1, further comprising a probe assembly comprising a first probe and a second probe.

8. The retractor of claim 1, further comprising a shim comprising an alignment feature, wherein at least one blade comprises a corresponding alignment feature.

9. The retractor of claim 1, wherein the first lock handle is biased to engage a pawl with the first actuator.

10. The retractor of claim 1, wherein the first lock handle pivots relative to the first actuator.

11. The retractor of claim 1, wherein the first lock handle comprises a pawl configured to directly engage the first actuator.

12. The retractor of claim 1, wherein the first lock handle is configured to limit the first blade from closing, while allowing the first blade to open along the first translation direction.

13. The retractor of claim 1, wherein the first blade and the second blade are configured to move in opposite directions to open the retractor.

14. The retractor of claim 1, wherein the first blade and the second blade are configured to nest when the retractor is in a closed position.

15. A method of using a retractor, comprising:

providing a retractor comprising a first blade assembly comprising a first blade and a first rack comprising a first toothed bar, a first actuator, a first lock handle, and second blade assembly comprising a second blade and a second rack comprising a second toothed bar, wherein the first rack and the second rack are aligned to translate along a common axis; and translating the first blade along a first translation direction with the first actuator, wherein the first lock handle limits translation along a direction opposite the first translation direction.

16. The method of claim 15, further comprising translating the second blade along a second translation direction with a second actuator.

17. The method of claim 15, further comprising inserting a first probe and a second probe toward an anatomical location.

18. The method of claim 17, further comprising inserting the second blade of the retractor over the first probe and the second probe.

19. The method of claim 18, further comprising removing the second probe and inserting a shim.

20. The method of claim 19, further comprising removing the first probe.

* * * * *